US011315275B2

(12) United States Patent
Addison et al.

(10) Patent No.: US 11,315,275 B2
(45) Date of Patent: Apr. 26, 2022

(54) EDGE HANDLING METHODS FOR ASSOCIATED DEPTH SENSING CAMERA DEVICES, SYSTEMS, AND METHODS

(71) Applicant: Covidien LP, Mansfield, MA (US)

(72) Inventors: Paul S. Addison, Edinburgh (GB); Dominique Jacquel, Edinburgh (GB); Philip Smit, Hamilton (GB)

(73) Assignee: Covidien LP, Mansfield, MA (US)

(*) Notice: Subject to any disclaimer, the term of this patent is extended or adjusted under 35 U.S.C. 154(b) by 273 days.

(21) Appl. No.: 16/750,502

(22) Filed: Jan. 23, 2020

(65) Prior Publication Data

US 2020/0242790 A1 Jul. 30, 2020

Related U.S. Application Data

(60) Provisional application No. 62/797,538, filed on Jan. 28, 2019.

(51) Int. Cl.
*G06T 7/579* (2017.01)
*G06T 7/11* (2017.01)
(Continued)

(52) U.S. Cl.
CPC ............ *G06T 7/579* (2017.01); *A61B 5/0816* (2013.01); *A61B 5/113* (2013.01);
(Continued)

(58) Field of Classification Search
CPC ... A61B 5/0064; A61B 5/0816; A61B 5/1128; A61B 5/113; A61B 5/1135; A61B 5/748;
(Continued)

(56) References Cited

U.S. PATENT DOCUMENTS 5,107,845 A 4/1992 Guern et al.
5,408,998 A 4/1995 Mersch
(Continued)

FOREIGN PATENT DOCUMENTS

CN 106725410 A 5/2017
CN 111728602 A 10/2020
(Continued)

OTHER PUBLICATIONS

Aarts, Lonneke A.M. et al., "Non-contact heart rate monitoring utilizing camera photoplethysmography in the neonatal intensive care unit—A pilot study", Early Human Development 89, 2013, pp. 943-948 (6 pp.).

(Continued)

*Primary Examiner* — Manuchehr Rahmjoo
(74) *Attorney, Agent, or Firm* — Holzer Patel Drennan

(57) ABSTRACT

The present technology relates to the field of medical monitoring, and, in particular, to non-contact detecting and monitoring of patient breathing. Systems, methods, and computer readable media are described for calculating a change in depth of a region of interest (ROI) on a patient. In some embodiments, the systems, methods, and/or computer readable media can identify steep changes in depths. For example, the systems, methods, and/or computer readable media can identify large, inaccurate changes in depths that can occur at edge regions of a patient. In these and other embodiments, the systems, methods, and/or computer readable media can adjust the identified steep changes in depth before determining one or more patient respiratory parameters.

19 Claims, 10 Drawing Sheets

(51) Int. Cl.
  *G06T 7/12* (2017.01)
  *A61B 5/08* (2006.01)
  *A61M 16/00* (2006.01)
  *A61B 5/113* (2006.01)

(52) U.S. Cl.
  CPC .......... *A61M 16/0072* (2013.01); *G06T 7/11* (2017.01); *G06T 7/12* (2017.01); *A61M 2230/42* (2013.01); *G06T 2207/20104* (2013.01); *G06T 2207/30196* (2013.01)

(58) Field of Classification Search
  CPC .......... A61B 5/7485; A61M 16/0072; A61M 2230/42; G06T 2207/10016; G06T 2207/10028; G06T 2207/20104; G06T 2207/30196; G06T 7/11; G06T 7/12; G06T 7/254; G06T 7/579; G16H 30/40
  See application file for complete search history.

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,668,071 | B1 | 12/2003 | Minkin et al. |
| 6,920,236 | B2 | 7/2005 | Prokoski |
| 7,431,700 | B2 | 10/2008 | Aoki et al. |
| 7,558,618 | B1 | 7/2009 | Williams |
| 8,149,273 | B2 | 4/2012 | Liu et al. |
| 8,754,772 | B2 | 6/2014 | Horng et al. |
| 8,792,969 | B2 | 6/2014 | Bernal et al. |
| 8,971,985 | B2 | 3/2015 | Bernal et al. |
| 9,226,691 | B2 | 1/2016 | Bernal et al. |
| 9,282,725 | B2 | 3/2016 | Jensen-Jarolim et al. |
| 9,301,710 | B2 | 4/2016 | Mestha et al. |
| 9,402,601 | B1 | 8/2016 | Berger et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,693,710 | B2 | 4/2017 | Mestha et al. |
| 9,697,599 | B2 | 4/2017 | Prasad et al. |
| 9,662,022 | B2 | 5/2017 | Kyal et al. |
| 9,693,693 | B2 | 7/2017 | Farag et al. |
| 9,750,461 | B1 | 9/2017 | Telfort |
| 9,839,756 | B2 | 12/2017 | Klasek |
| 9,943,371 | B2 | 4/2018 | Bresch et al. |
| 10,398,353 | B2 | 9/2019 | Addison et al. |
| 10,523,852 | B2 | 12/2019 | Tzvieli et al. |
| 10,588,779 | B2 | 3/2020 | Vorhees et al. |
| 10,667,723 | B2 | 6/2020 | Jacquel et al. |
| 10,702,188 | B2 | 7/2020 | Addison et al. |
| 10,874,331 | B2 | 12/2020 | Kaiser et al. |
| 10,939,824 | B2 | 3/2021 | Addison et al. |
| 10,939,834 | B2 | 3/2021 | Khwaja et al. |
| 2004/0001633 | A1 | 1/2004 | Caviedes |
| 2004/0258285 | A1 | 12/2004 | Hansen et al. |
| 2005/0203348 | A1 | 9/2005 | Shihadeh et al. |
| 2007/0116328 | A1 | 5/2007 | Sablak et al. |
| 2008/0001735 | A1 | 1/2008 | Tran |
| 2008/0279420 | A1 | 11/2008 | Masticola et al. |
| 2008/0029583 | A1 | 12/2008 | McCormick et al. |
| 2008/0295837 | A1 | 12/2008 | McCormick et al. |
| 2009/0304280 | A1 | 12/2009 | Ahroni et al. |
| 2010/0236553 | A1 | 9/2010 | Jafari et al. |
| 2010/0249630 | A1 | 9/2010 | Droitcour et al. |
| 2010/0324437 | A1 | 12/2010 | Freeman et al. |
| 2011/0144517 | A1 | 6/2011 | Cervantes |
| 2011/0150274 | A1 | 6/2011 | Patwardhan et al. |
| 2012/0075464 | A1 | 3/2012 | Derenne |
| 2012/0065533 | A1 | 5/2012 | Carrillo, Jr. et al. |
| 2012/0243797 | A1 | 9/2012 | Di Venuto Dayer et al. |
| 2013/0271591 | A1 | 10/2013 | Van Leest et al. |
| 2013/0272393 | A1 | 10/2013 | Kirenko et al. |
| 2013/0275873 | A1 | 10/2013 | Shaw et al. |
| 2013/0324830 | A1 | 12/2013 | Bernal et al. |
| 2013/0324876 | A1 | 12/2013 | Bernal et al. |
| 2014/0023235 | A1 | 1/2014 | Cennini et al. |
| 2014/0052006 | A1 | 2/2014 | Lee et al. |
| 2014/0053840 | A1 | 2/2014 | Liu |
| 2014/0267718 | A1 | 9/2014 | Govro et al. |
| 2014/0272860 | A1 | 9/2014 | Peterson et al. |
| 2014/0275832 | A1 | 9/2014 | Muehlsteff et al. |
| 2014/0276104 | A1 | 9/2014 | Tao et al. |
| 2014/0330336 | A1 | 11/2014 | Errico et al. |
| 2014/0358017 | A1 | 12/2014 | Op Den Buijs et al. |
| 2014/0378810 | A1 | 12/2014 | Davis et al. |
| 2014/0379369 | A1 | 12/2014 | Kokovidis et al. |
| 2015/0003723 | A1 | 1/2015 | Huang et al. |
| 2015/0131880 | A1 | 5/2015 | Wang et al. |
| 2015/0157269 | A1 | 6/2015 | Lisogurski et al. |
| 2015/0238150 | A1 | 8/2015 | Subramaniam |
| 2015/0265187 | A1* | 9/2015 | Bernal ............... A61B 5/1128 600/474 |
| 2015/0282724 | A1 | 10/2015 | McDuff et al. |
| 2015/0301590 | A1 | 10/2015 | Furst et al. |
| 2015/0317814 | A1 | 11/2015 | Johnston et al. |
| 2016/0000335 | A1 | 1/2016 | Khachaturian et al. |
| 2016/0049094 | A1 | 2/2016 | Gupta et al. |
| 2016/0082222 | A1 | 3/2016 | Garcia Molina et al. |
| 2016/0143598 | A1 | 5/2016 | Rusin et al. |
| 2016/0151022 | A1 | 6/2016 | Berlin et al. |
| 2016/0156835 | A1 | 6/2016 | Ogasawara et al. |
| 2016/0174887 | A1 | 6/2016 | Kirenko |
| 2016/0310084 | A1 | 10/2016 | Banarjee et al. |
| 2016/0317041 | A1 | 11/2016 | Porges et al. |
| 2016/0345931 | A1 | 12/2016 | Xu et al. |
| 2017/0007342 | A1 | 1/2017 | Kasai et al. |
| 2017/0007795 | A1 | 1/2017 | Pedro et al. |
| 2017/0055877 | A1 | 3/2017 | Niemeyer |
| 2017/0065484 | A1 | 3/2017 | Addison et al. |
| 2017/0095217 | A1 | 4/2017 | Hubert et al. |
| 2017/0119340 | A1 | 5/2017 | Nakai et al. |
| 2017/0147772 | A1 | 5/2017 | Meehan et al. |
| 2017/0164904 | A1 | 6/2017 | Kirenko |
| 2017/0238805 | A1 | 8/2017 | Addison et al. |
| 2017/0238842 | A1 | 8/2017 | Jacquel et al. |
| 2017/0319114 | A1 | 11/2017 | Kaestle |
| 2018/0042486 | A1 | 2/2018 | Yoshizawa et al. |
| 2018/0042500 | A1 | 2/2018 | Liao et al. |
| 2018/0053392 | A1 | 2/2018 | White et al. |
| 2018/0104426 | A1 | 4/2018 | Oldfield et al. |
| 2018/0106897 | A1 | 4/2018 | Shouldice et al. |
| 2018/0169361 | A1 | 6/2018 | Dennis |
| 2018/0217660 | A1 | 8/2018 | Dayal et al. |
| 2018/0228381 | A1 | 8/2018 | Leboeuf et al. |
| 2018/0310844 | A1 | 11/2018 | Tezuka et al. |
| 2018/0325420 | A1 | 11/2018 | Gigi |
| 2018/0333050 | A1 | 11/2018 | Greiner et al. |
| 2019/0050985 | A1 | 2/2019 | Den Brinker et al. |
| 2019/0142274 | A1 | 5/2019 | Addison et al. |
| 2019/0209046 | A1 | 7/2019 | Addison et al. |
| 2019/0209083 | A1 | 7/2019 | Wu et al. |
| 2019/0307365 | A1 | 10/2019 | Addison et al. |
| 2019/0343480 | A1 | 11/2019 | Shute et al. |
| 2019/0380599 | A1 | 12/2019 | Addison et al. |
| 2019/0380807 | A1 | 12/2019 | Addison et al. |
| 2020/0046302 | A1 | 2/2020 | Jacquel et al. |
| 2020/0187827 | A1 | 6/2020 | Addison et al. |
| 2020/0237225 | A1 | 7/2020 | Addison et al. |
| 2020/0289024 | A1 | 9/2020 | Addison et al. |
| 2020/0329976 | A1 | 10/2020 | Chen et al. |
| 2021/0068670 | A1 | 3/2021 | Redtel |
| 2021/0153746 | A1 | 5/2021 | Addison et al. |

FOREIGN PATENT DOCUMENTS

| | | |
|---|---|---|
| CN | 112233813 A | 1/2021 |
| DE | 19741982 A1 | 10/1998 |
| EP | 2428162 A1 | 3/2012 |
| EP | 2772828 A1 | 9/2014 |
| EP | 2793189 A2 | 10/2014 |
| EP | 3207862 A1 | 8/2017 |
| EP | 3207863 A1 | 8/2017 |

(56) References Cited

FOREIGN PATENT DOCUMENTS

| EP | 3384827 A1 | 10/2018 |
|---|---|---|
| JP | 2009544080 A | 12/2009 |
| JP | 2011130996 A | 7/2011 |
| KR | 101644843 B1 | 8/2016 |
| WO | 2004100067 A2 | 11/2004 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

Addison, Paul S. et al., "Pulse oximetry-derived respiratory rate in general care floor patients", J Clin Monit Comput, 2015, 29, pp. 113-120 (8 pp.).
Bousefsaf, Frederic, et al., "Continuous wavelet filtering on webcam photoplethysmographic signals to remotely assess the instantaneous heart rate", Biomedical Signal Processing and Control 8, 2013, pp. 568-574.
BSI Standards Publication, "Medical electrical equipment, Part 2-61: Particular requirements for basic safety and essential performance of pulse oximeter equipment", BS EN ISO 80601-2-61:2011, 98 pgs.
European Search Report for European Application No. 17156334.9; Applicant: Covidien LP; dated Jul. 13, 2017, 10 pages.
European Search Report; European Patent Application No. 17156337.2; Applicant: Covidien LP; dated Jul. 13, 2017, 10 pages.
Guazzi, Alessandro R., et al., "Non-contact measurement of oxygen saturation with an RGB camera", Biomedical Optics Express, Sep. 1, 2015, vol. 6, No. 9, pp. 3320-3338 (19 pp.).
International Application No. PCT/US2019/035433 Invitation to Pay Additional Fees and Partial International Search Report dated Sep. 13, 2019, 16 pages (MD60009PCT).
International Application No. PCT/US2019/045600 International Search Report and Written Opinion dated Oct. 23, 2019, 19 pages (MD60002PCT).
International Search Report and Written Opinion for International Application No. PCT/US2018/060648, dated Jan. 28, 2019, 17 pages.
International Search Report and Written Opinion for International Application No. PCT/US2018/065492, dated Mar. 8, 2019, 12 pages.
Jopling, Michael W., et al., "Issues in the Laboratory Evaluation of Pulse Oximeter Performance", Anesth. Analg. 2002; 94, pp. S62-S68 (7 pp.).
Kong, Lingqin, et al., "Non-contact detection of oxygen saturation based on visible light imaging device using ambient light", Optics Express, Jul. 29, 2013, vol. 21, No. 15, pp. 17464-17471 (8 pp.).
Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177 (4 pp.).
Litong Feng, et al. Dynamic ROI based on K-means for remote photoplethysmography, IEEE International Conference on Accoustics, Speech and Signal Processing (ICASSP), Apr. 2015, p. 1310-1314 (Year: 2015) (5 pp.).

Nguyen, et al., "3D shape, deformation and vibration measurements using infrared Kinect sensors and digital image correlation", Applied Optics, vol. 56, No. 32, Nov. 8, 2017, 8 pages.
Povsi, et al., Real-Time 3D visualization of the thoraco-abdominal surface during breathing with body movement and deformation extraction, Physiological Measurement, vol. 36, No. 7, May 28, 2015, pp. 1497-1516.
Prochazka et al., "Microsoft Kinect Visual and Depth Sensors for Breathing and Heart Rate Analysis", Sensors, vol. 16, No. 7, Jun. 28, 2016, 11 pages.
Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622 (12 pp.).
Schaerer, et al., "Multi-dimensional respiratory motion tracking from markerless optical surface imaging based on deformable mesh registration", Physics in Medicine and Biology, vol. 57, No. 2, Dec. 14, 2011, 18 pages.
Shah, Nitin, et al., "Performance of three new-generation pulse oximeters during motion and low perfursion in volunteers", Journal of Clinical Anesthesia, 2012, 24, pp. 385-391 (7 pp.).
Shao, Dangdang, et al., "Noncontact Monitoring Breathing Pattern, Exhalation Flow Rate and Pulse Transit Time", IEEE Transactions on Biomedical Engineering, vol. 61, No. 11, Nov. 2014, pp. 2760-2767 (8 pp.).
Sun, Yu, et al., "Noncontact imaging photoplethysmography to effectively access pulse rate variability", Journal of Biomedical Optics, Jun. 2013, vol. 18(6), 10 pages.
Tarassenko, L. et al., "Non-contact video-based vital sign monitoring using ambient light and auto-regressive models", Institute of Physics and Engineering in Medicine, 2014, pp. 807-831 (26 pp.).
Villarroel, Mauricio, et al., "Continuous non-contact vital sign monitoring in neonatal intensive care unit", Healthcare Technology Letters, 2014, vol. 1, Iss 3, pp. 87-91.
Zaunseder, et al. "Spatio-temporal analysis of blood perfusion by imaging photoplethysmography," Progress in Biomedical Optics and Imaging, SPIE—International Society for Optical Engineering, vol. 10501, Feb. 20, 2018, 15 pages.
Barone, et al., "Computer-aided modelling of three-dimensional maxillofacial tissues through multi-modal imaging", Journal of Engineering in Medicine, Part H. vol. 227, No. 2, Feb. 1, 2013, pp. 89-104.
Barone, et al., "Creation of 3D Multi-body Orthodontic Models by Using Independent Imaging Sensors", Senros MDPI AG Switzerland, vol. 13, No. 2, Jan. 1, 2013, pp. 2033-2050.
Hyvarinen, A. et al., "Independent Component Analysis: Algorithms and Applications", Neural Networks, vol. 13, No. 4, 2000, pp. 411-430, 31 pages.
International Search Report and Written Opinion for International Application No. PCT/US19/035433, dated Nov. 11, 2019, 17 pages.
Abbas A. K. et al., "Neonatal non-contact respiratory monitoring based on real-time infrared thermography," Biomed. Eng. Online, vol. 10, No. 93, 2011, 17 pages.
Addison, P. S. et al., "Video-based Heart Rate Monitoring across a Range of Skin Pigmentations during an Acute Hypoxic Challenge," J Clin Monit Comput, Nov. 9, 2017, 10 pages.
Addison, Paul S. et al., "Developing an algorithm for pulse oximetry derived respiratory rate (RRoxi): a healthy volunteer study", J Clin Comput (2012) 26, pp. 45-51.
Addison, Paul S. PhD., "A Review of Signal Processing Used in the Implemenation of the Pulse Oximetry Phtoplethysmographic Fluid Responseiveness Parameter", International Anesthesia Research Society, Dec. 2014, vol. 119, No. 6, pp. 1293-1306.
Amelard et al., "Non-contact transmittance photoplethysmographic imaging (PPGI) for long-distance cardiovascular monitoring," ResearchGate, Mar. 23, 2015, pp. 1-13, XP055542534 [Retrieved online Jan. 15, 2019].
Bhattacharya, S. et al., "A Noevel Classification Method for Predicting Acute Hypotenisve Episodes in Critical Care," 5th ACM Conference on Bioinformatics, Computational Biology and Health Informatics (ACM-BCB 2014), Newport Beach, USA, 2014, 10 pages.

(56) References Cited

OTHER PUBLICATIONS

Bhattacharya, S. et al., "Unsupervised learning using Gaussian Mixture Copula models," 21st International Conference on Computational Statistics (COMPSTAT 2014), Geneva, Switzerland, 2014, 8 pages.
Bickler, Philip E. et al., "Factors Affecting the Performance of 5 Cerebral Oximeters During Hypoxia in Healthy Volunteers", Society for Technology in Anesthesia, Oct. 2013, vol. 117, No. 4, pp. 813-823.
Bruser, C. et al., "Adaptive Beat-to-Beat Heart Rate Estimation in Ballistocardiograms," IEEE Transactions Information Technology in Biomedicine, vol. 15, No. 5, Sep. 2011, pp. 778-786.
Cennini, Giovanni, et al., "Heart rate monitoring via remote phtoplethysmography with motion artifacts reduction", Optics Express, Mar. 1, 2010, vol. 18, No. 5, pp. 4867-4875.
Colantonio, S., "A smart mirror to promote a healthy lifestyle," Biosystems Engineering, vol. 138, Oct. 2015, pp. 33-34, Innovations in Medicine and Healthcare.
Cooley et al. "An Algorithm for the Machine Calculation of Complex Fourier Series," Aug. 17, 1964, pp. 297-301.
Fei J. et al., "Thermistor at a distance: unobstrusive measurement of breathing," IEEE Transactions on Biomedical Engineering, vol. 57, No. 4, pp. 968-998, 2010.
George et al., "Respiratory Rate Measurement From PPG Signal Using Smart Fusion Technique," International Conference on Engineering Trends and Science & Humanities (ICETSH-2015), 5 pages, 2015.
Goldman, L. J., "Nasal airflow and thoracoabdominal motion in children using infrared thermographic video processing," Pediatric Pulmonology, vol. 47, No. 5, pp. 476-486, 2012.
Han, J. et al., "Visible and infrared image registration in man-made environments employing hybrid visuals features," Pattern Recognition Letters, vol. 34, No. 1, pp. 42-51, 2013.
Huddar, V. et al., "Predicting Postoperative Acute Respiratory Failure in Critical Care using Nursing Notes and Physiological Signals," 36th Annual International Conference of IEEE Engineering in Medicine and Biology Society (IEEE EMBC 2014) Chicago, USA, 2014, 4 pages.
Javadi M. et al., "Diagnosing Pneumonia in Rural Thailand: Digital Cameras versus Film Digitizers For Chest Radiogrpah Teleradiology," International Journal of Infectious Disease, Mar. 2006; 10(2), pp. 129-135.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552.
Klaessens J. H. G. M. et al., "Non-invasive skin oxygenation imaging using a multi-spectral camera system: Effectiveness of various concentration algorithms applied on human skin," Proc. of SPIE vol. 7174 717408-1, 2009, 14 pages.
Kortelainen, J. et al. "Sleep staging based on signals acquired through bed sensor," IEEE Transactions on Information Technology in Biomedicine, vol. 14, No. 3, pp. 776-785, 2010.
Kumar, M. et al., "Distance PPG: Robust non-contact vital signs monitoring using a camera," Biomedical Optics Express, 2015, 24 pages.
Lai, C. J. et al. "Heated humidified high-flow nasal oxygen prevents intraoperative body temperature decrease in non-intubated thoracoscopy". Journal of Anesthesia. Oct. 15, 2018. 8 pages.
Li et al., "A Non-Contact Vision-Baed System for Respiratory Rate Estimation", 978-1-4244-7929-0/14, 2014, 4 pages.
Liu, C. et al., "Motion Magnification," ACM Transactions on Graphics (TOG), vol. 24, No. 3, pp. 519-526, 2005.
Liu, H. et al., "A Novel Method Based on Two Cameras For Accurate Estimation of Arterial Oxygen Saturation," BioMedical Engineering OnLine, 2015, 17 pages.
Lv et al., "Class Energy Image Analysis for Video Sensor-Based Gait Recognition: A Review", Sensors 2015, 15, pp. 932-964.
McDuff, Daniel J. et al., "A Survey of Remote Optical Photoplethysmographic Imaging Methods", 987-1-4244-9270-1/15, IEEE, 2015, pp. 6398-6404.
Mestha, L.K. et al., "Towards Continuous Monitoring of Pulse Rate in Neonatal Intensive Care Unit with a Webcam," in Proc. of 36th Annual Int. conf. of the IEEE Engineering in Medicine and Biology Society, Chicago, Il, pp. 1-5, 2014.
Ni et al. "RGBD-Camera Based Get-Up Event Detection for Hospital Fall Prevention." Acoustics, Speech and Signal Processing (ICASSP). 2012 IEEE International Conf., Mar. 2012, pp. 1405-1408.
Nisar et al. "Contactless heart rate monitor for multiple persons in a video", IEEE International Conference on Consumer Electronics—Taiwan (ICCE-TW), May 27, 2016, pp. 1-2, XP032931229 [Retrieved on Jul. 25, 2016].
Pereira, C. et al. "Noncontact Monitoring of Respiratory Rate in Newborn Infants Using Thermal Imaging." IEEE Transactions on Biomedical Engineering. Aug. 23, 2018. 10 Pages.
Poh et al., "Non-contact, automated cardiac pulse measurements using video imaging and blind source separation," OPT. Express 18, 10762-10774 (2010), 14 pages.
Poh, et al., "Advancements in Noncontact, Multiparameter Physiological Measurements Using a Webcam", IEEE Transactions on Biomedical Engineering, vol. 58, No. 1, Jan. 2011, 5 pages.
Rajan, V. et al. "Dependency Clustering of Mixed Data with Gaussian Mixture Copulas," 25th International Joint Conference on Artificial Intelligence IJCAI 2016, New York, USA, 7 pages.
Rajan, V. et al., "Clincal Decision Support for Stroke using MultiviewLearning based Models for NIHSS Scores," PAKDD 2016 Workshop: Predictive Analytics in Critical Care (PACC), Auckland, New Zealand, 10 pages.
Reisner, A, et al., "Utility of the Photoplethysmogram in Circulatory Monitoring," American Society of Anesthesiolgist, May 2008, pp. 950-958.
Rubinstein, M., "Analysis and Visualization of Temporal Variations in Video", Department of Electrical Engineering and Computer Science, Massachusetts Institute of Technology, Feb. 2014, 118 pages.
Scalise, Lorenzo, et al., "Heart rate measurement in neonatal patients using a webcamera," 978-1-4673-0882-3/12, IEEE, 2012, 4 pages.
Sengupta, A. et al., "A Statistical Model for Stroke Outcome Prediction and Treatment Planning," 38th Annual International Conference of the IEE Engineering in Medicine and Biology (Society IEEE EMBC2016), Orlando, USA, 2016, 4 pages.
Shrivastava, H. et al., "Classification with Imbalance: A Similarity-based Method for Predicting Respiratory Failure," 2015 IEEE International Conference on Bioinformatics and Biomedicine (IEEE BIBM2015), Washington DC, USA, 8 pages.
Tamura et al., "Wearable Photoplethysmographic Sensors—Past & PResent," Electronics, 2014, pp. 282-302.
Teichmann, D. et al., "Non-contact monitoring techniques—Principles and applications," In Proc. of IEEE International Conference of the Engineering in Medicine and Biology Society (EMBC), San Diego,CA, 2012, 4 pages.
Verkruysee, Wim, et al., "Calibration of Contactless Pulse Oximetry", Anesthesia & Analgesia, Jan. 2017, vol. 124, No. 1, pp. 136-145.
Wadhwa, N. et al., "Phase-Based Video Motion Processing," MIT Computer Science and Artificial Intelligence Lab, Jul. 2013, 9 pages.
Wadhwa, N. et al., "Riesz pyramids for fast phase-based video magnification." In Proc. of IEEE International Conference on Computational Photography (ICCP), Santa Clara, CA, pp. 1-10, 2014.
Wang, W. et al., "Exploiting spatial redundancy of image sensor for motion robust rPPG." IEEE Transactions on Biomedical Engineering, vol. 62, No. 2, pp. 415-425, 2015.
Wu, H.Y. et al.,"Eulerian video magnification for recealing subtle changes in the world," ACM Transactions on Graphics (TOG), vol. 31, No. 4, pp. 651-658, 2012.

(56) References Cited

OTHER PUBLICATIONS

Yu et al. "Motion-compensated noncontact imaging photoplethysmography to monitor cardiorespiratory status during exercise," Journal of Biomedical Optics, vol. 16, No. 7, Jan. 1, 2011, 10 pages.

Zhou, J. et al., "Maximum parsimony analysis of gene copy number changes in tumor phylogenetics," 15th International Workshop on Algorithms in Bioinformatics WABI 2015, Atlanta, USA, 13 pages.

Armanian, A. M., "Caffeine administration to prevent apnea in very premature infants", Pediatrics & Neonatology, 57(5), 2016, pp. 408-412, 5 pages.

Di Fiore, J.M., et al., "Intermittent hypoxemia and oxidative stress in preterm infants", Respiratory Physiology & Neurobiology, No. 266, 2019, pp. 121-129, 25 pages.

Grimm, T., et al., "Sleep position classification from a depth camera using bed aligned maps", 23rd International Conference on Pattern Recognition (ICPR), Dec. 2016, pp. 319-324, 6 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

\* cited by examiner

EDGE HANDLING METHODS FOR ASSOCIATED DEPTH SENSING CAMERA DEVICES, SYSTEMS, AND METHODS

CROSS-REFERENCE TO RELATED APPLICATIONS

This application claims priority to U.S. Provisional Patent Application Ser. No. 62/797,538, filed Jan. 28, 2019, the entire contents of which are incorporated herein by reference.

FIELD

The present technology is generally related to patient monitoring using an image capture device and edge handling methods therefor.

BACKGROUND

Many conventional medical monitors require attachment of a sensor to a patient in order to detect physiologic signals from the patient and to transmit detected signals through a cable to the monitor. These monitors process the received signals and determine vital signs such as the patient's pulse rate, respiration rate, and arterial oxygen saturation. For example, a pulse oximeter is a finger sensor that can include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a field of patient monitoring that uses one or more remote video cameras to detect physical attributes of the patient. This type of monitoring can also be called "non-contact" monitoring in reference to the remote video sensor(s), which does/do not contact the patient. The remainder of this disclosure offers solutions and improvements in this field.

SUMMARY

The techniques of this disclosure generally relate to systems and methods for patient monitoring using an image capture device, including defining a region of interest (ROI) on a patient; capturing two or more images of the ROI using an image capture device; calculating an overall change in depth of the ROI within the two or more images, wherein calculating the overall change in depth of the ROI includes: measuring changes in depths of portions of the ROI; recognizing steep changes in depths in the measured changes in depths; and adjusting the recognized steep changes in depths.

In another aspect, adjusting the recognized steep changes in depths includes excluding the recognized steep changes in depths from the calculation of the overall change in depth of the ROI.

In another aspect, adjusting the recognized steep changes in depths includes (i) excluding measured changes in depths corresponding to an outer percentage of the ROI and/or to an edge region of the patient and/or (ii) excluding a percentage of the measured changes in depths surrounding a recognized steep change in depth.

In another aspect, adjusting the recognized steep changes in depths comprises including only measured changes in depths up to and/or between one or more recognized steep changes in depths in the calculation of the overall change in depth of the ROI.

In another aspect, adjusting the recognized steep changes in depths includes interpolating and/or extrapolating over the recognized steep changes in depths using one or more other measured changes in depths.

In another aspect, adjusting the recognized steep changes in depths includes using a template to approximate changes in depths at portions of the ROI corresponding to the recognized steep changes in depths.

Other aspects include determining one or more patient respiratory parameters using all or a subset of the measured changes in depths and/or all or a subset of the adjusted changes in depths. An exemplary patient respiratory parameter includes a tidal volume of the patient, and wherein the tidal volume of the patient is determined using a subset of the measured changes in depths excluding the recognized steep changes in depths and/or all or a subset of the adjusted changes in depths. Another exemplary patient respiratory parameters includes a respiratory rate of the patient, wherein the respiratory rate of the patient is determined using all of the measured changes in depths and none of the adjusted changes in depths.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1:
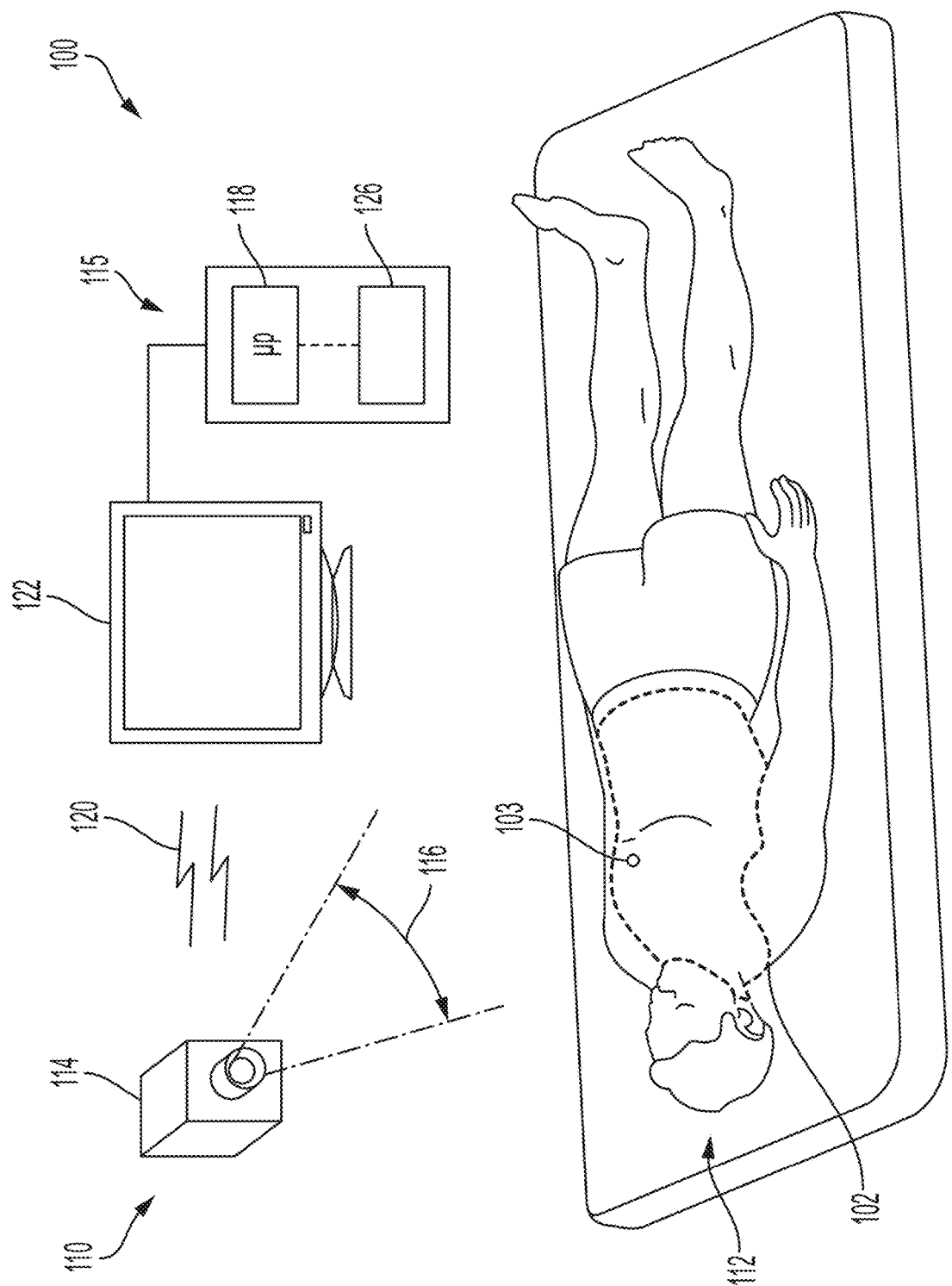
FIG. 1 is a schematic view of a video-based patient monitoring system configured in accordance with various embodiments of the present technology.

The following disclosure describes video-based patient monitoring devices, systems, and associated methods for mitigating errors in changes in depths measured at edges of a patient (e.g., at edges of a patient's torso). As described in greater detail below, devices, systems, and/or methods configured in accordance with embodiments of the present technology are configured to capture one or more images (e.g., a video sequence) of a patient or portion(s) of a patient (e.g., a patient's torso) within a field of view of an image capture device. The devices, systems, and/or methods can measure changes in depths of regions (e.g., one or more pixels or groups of pixels) in the captured images over time. Based, at least in part, on these measurements, the devices, systems, and/or methods can determine various respiratory parameters of a patient, including tidal volume, minute volume, respiratory rate, among others. In these and other embodiments, the device, systems, and/or methods can analyze the respiratory parameters and can trigger alerts and/or alarms when the devices, systems, and/or methods detect one or more breathing abnormalities.

Errors in measured depths and/or changes in depths can occur at edges of a patient within the field of view of the image capture device. For example, lateral movement of a patient's torso at the edges of the patient's torso can be perceived as large changes in depths of the patient's torso in these regions. Additionally, or alternatively, as a patient inhales and exhales, edge portions of the patient's torso can move within and outside a line of sight of an image capture device. Thus, during a first portion of the patient's respiratory cycle (e.g., during a portion in which the patient's lungs contain greater than or equal to a first volume of air), an edge portion of the patient's torso can move within and/or remain within the line of sight of the image capture device. During a second portion of the patient's respiratory cycle (e.g., during a portion in which the patient's lungs contain less than or equal to the first volume of air), the edge portion of the patient's torso can move outside or and/or remain outside of the line of sight of the image capture device. As a result, the image capture device can perceive large, inaccurate changes in depths at edge regions of the patient at various points throughout the patient's respiratory cycle. These large, inaccurate changes in depths can contribute to errors in the respiratory parameters of the patient determined by the video-based patient monitoring devices, system, and/or methods.

Therefore, the video-based patient monitoring devices, systems, and associated methods of the present technology are configured to mitigate the errors in changes in depths measured at edge regions of a patient (e.g., of a patient's torso). In some embodiments, the devices, systems, and associated methods exclude the edge portions while integrating over a region within the extent of the patient. In these and other embodiments, the devices, systems, and associated methods interpolate changes in depths at the edge regions using changes in depths perceived at other regions of the patient. In these and still other embodiments, the device, systems, and associated methods use a template (e.g., a template generated from a previous scan of the patient) to estimate changes in depths that occur at the edge regions of the patient. In this manner, the video-based patient monitoring devices, systems, and associated methods configured in accordance with various embodiments of the present technology can more accurately measure changes in depths that occur at edge regions of a patient within the field of view of the image capture device(s). In turn, the devices, systems, and associated methods can more accurately determine a patient's respiratory parameters.

Specific details of several embodiments of the present technology are described herein with reference to FIGS. 1-9. Although many of the embodiments are described with respect to devices, systems, and methods for video-based detection and/or monitoring of breathing in a human patient, other applications and other embodiments in addition to those described herein are within the scope of the present technology. For example, at least some embodiments of the present technology can be useful for video-based detection and/or monitoring of breathing in other animals and/or in non-patients (e.g., elderly or neonatal individuals within their homes). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "steep" shall be understood to include any change in depth or rate of change above a threshold value or percentage. In some embodiments, the threshold value or percentage can be a predetermined and/or predefined threshold value (e.g., 0.5 mm, 1 mm, 2 mm, 5 mm, 10 mm, 20 mm, 50 mm, 75 mm, 100 mm, etc.) or percentage (e.g., 1%, 2%, 5%, 10%, 20%, 30%, 40%, 50%, 60%, 70%, 80%, 90%, 95%, 97%, etc.). In these and other embodiments, the term "steep" shall be understood to encompass any change in depth or rate of change above a threshold value or percentage vis-à-vis the same pixel and/or region of an ROI across two or more images. In these and still other embodiments, the term "steep" shall be understood to encompass any change in depth or rate of change above a threshold value or percentage vis-à-vis neighboring and/or adjacent pixels and/or regions of an ROI across one or more images.

FIG. 1 is a schematic view of a patient 112 and a video-based patient monitoring system 100 configured in accordance with various embodiments of the present technology. The system 100 includes a non-contact detector 110 and a computing device 115. In some embodiments, the detector 110 can include one or more image capture devices, such as one or more video cameras. In the illustrated embodiment, the non-contact detector 110 includes a video camera 114. The non-contact detector 110 of the system 100 is placed remote from the patient 112. More specifically, the video camera 114 of the non-contact detector 110 is positioned remote from the patient 112 in that it is spaced apart from and does not contact the patient 112. The camera 114 includes a detector exposed to a field of view (FOV) 116 that encompasses at least a portion of the patient 112.

The camera 114 can capture a sequence of images over time. The camera 114 can be a depth sensing camera, such as a Kinect camera from Microsoft Corp. (Redmond, Wash.). A depth sensing camera can detect a distance between the camera and objects within its field of view. Such information can be used, as disclosed herein, to determine that a patient 112 is within the FOV 116 of the camera 114 and/or to determine one or more ROI's to monitor on the patient 112. Once a ROI is identified, the ROI can be monitored over time, and the changes in depths of regions (e.g., pixels) within the ROI 102 can represent movements of the patient 112 associated with breathing. As described in greater detail in U.S. patent application Ser. No. 16/219,360 and U.S. Provisional Patent Application Ser. No. 62/779,964, those movements, or changes of regions within the ROI 102, can be used to determine various breathing parameters, such as tidal volume, minute volume, respiratory rate, etc. Those movements, or changes of regions within the ROI 102, can also be used to detect various breathing abnormalities, as discussed in greater detail in U.S. Provisional Patent Application Ser. Nos. 62/716,724 and 62/779,964. The various breathing abnormalities can include, for example, apnea, rapid breathing (tachypnea), slow breathing, intermittent or irregular breathing, shallow breathing, obstructed and/or impaired breathing, and others. The entire disclosures of U.S. patent application Ser. No. 16/219,360 and U.S. Provisional Patent Application Ser. Nos. 62/716,724 and 62/779,964 are incorporated herein by reference.

In some embodiments, the system 100 determines a skeleton-like outline of the patient 112 to identify a point or points from which to extrapolate a ROI. For example, a skeleton-like outline can be used to find a center point of a chest, shoulder points, waist points, and/or any other points on a body of the patient 112. These points can be used to determine one or more ROI's. For example, a ROI 102 can be defined by filling in area around a center point 103 of the chest, as shown in FIG. 1. Certain determined points can define an outer edge of the ROI 102, such as shoulder points. In other embodiments, instead of using a skeleton, other points are used to establish a ROI. For example, a face can be recognized, and a chest area inferred in proportion and spatial relation to the face. In other embodiments, a reference point of a patient's chest can be obtained (e.g., through a previous 3-D scan of the patient), and the reference point can be registered with a current 3-D scan of the patient. In these and other embodiments, the system 100 can define a ROI around a point using parts of the patient 112 that are within a range of depths from the camera 114. In other words, once the system 100 determines a point from which to extrapolate a ROI, the system 100 can utilize depth information from the depth sensing camera 114 to fill out the ROI. For example, if the point 103 on the chest is selected, parts of the patient 112 around the point 103 that are a similar depth from the camera 114 as the point 103 are used to determine the ROI 102.

In another example, the patient 112 can wear specially configured clothing (not shown) that includes one or more features to indicate points on the body of the patient 112, such as the patient's shoulders and/or the center of the patient's chest. The one or more features can include visually encoded message (e.g., bar code, QR code, etc.), and/or brightly colored shapes that contrast with the rest of the patient's clothing. In these and other embodiments, the one or more features can include one or more sensors that are configured to indicate their positions by transmitting light or other information to the camera 114. In these and still other embodiments, the one or more features can include a grid or another identifiable pattern to aid the system 100 in recognizing the patient 112 and/or the patient's movement. In some embodiments, the one or more features can be stuck on the clothing using a fastening mechanism such as adhesive, a pin, etc. For example, a small sticker can be placed on a patient's shoulders and/or on the center of the patient's chest that can be easily identified within an image captured by the camera 114. The system 100 can recognize the one or more features on the patient's clothing to identify specific points on the body of the patient 112. In turn, the system 100 can use these points to recognize the patient 112 and/or to define a ROI.

In some embodiments, the system 100 can receive user input to identify a starting point for defining a ROI. For example, an image can be reproduced on a display 122 of the system 100, allowing a user of the system 100 to select a patient 112 for monitoring (which can be helpful where multiple objects are within the FOV 116 of the camera 114) and/or allowing the user to select a point on the patient 112 from which a ROI can be determined (such as the point 103 on the chest of the patient 112). In other embodiments, other methods for identifying a patient 112, identifying points on the patient 112, and/or defining one or more ROI's can be used.

Figure 2:
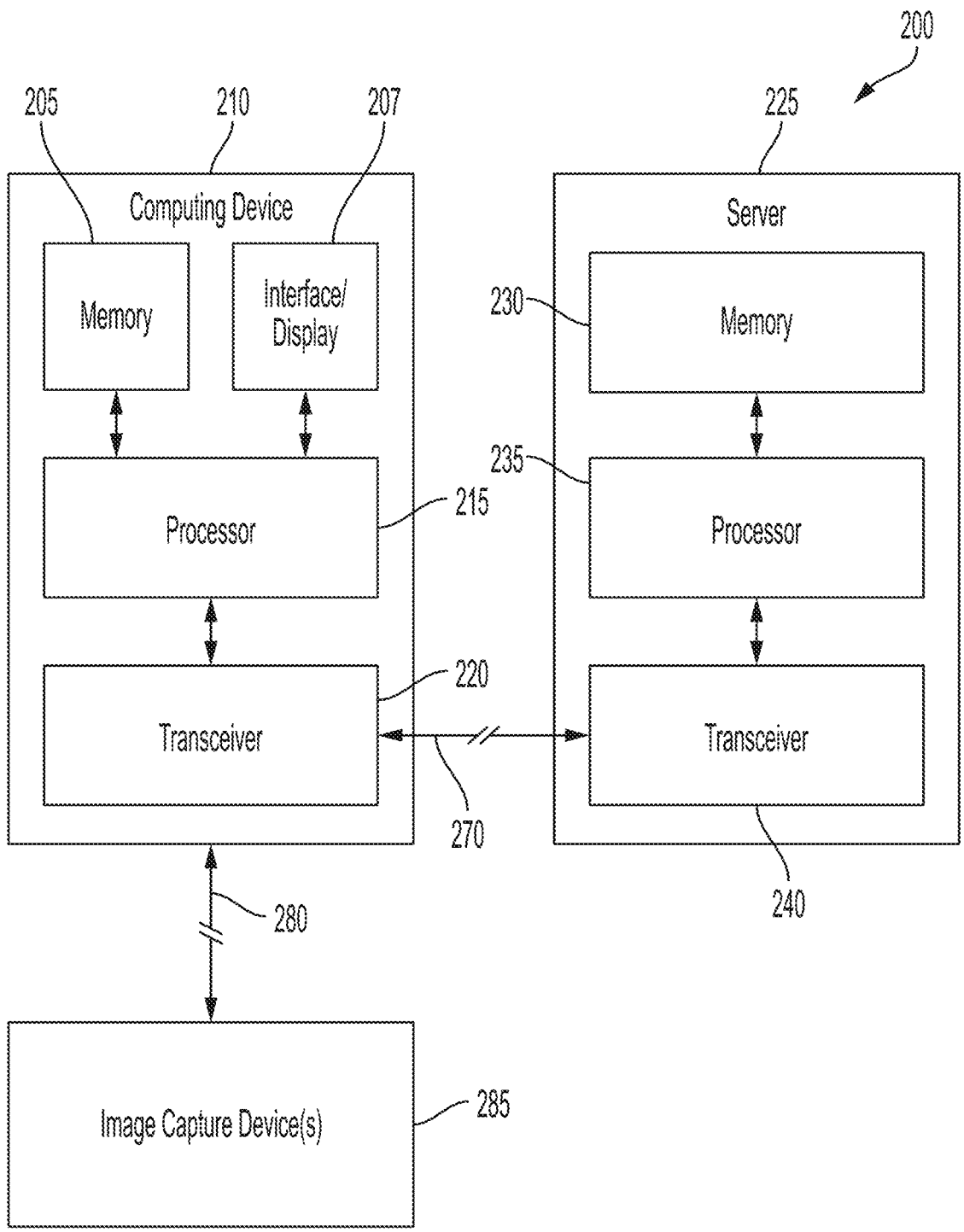
FIG. 2 is a block diagram illustrating a video-based patient monitoring system having a computing device, a server, and one or more image capture devices, and configured in accordance with various embodiments of the present technology.

The images detected by the camera 114 can be sent to the computing device 115 through a wired or wireless connection 120. The computing device 115 can include a processor 118 (e.g., a microprocessor), the display 122, and/or hardware memory 126 for storing software and computer instructions. Sequential image frames of the patient 112 are recorded by the video camera 114 and sent to the processor 118 for analysis. The display 122 can be remote from the camera 114, such as a video screen positioned separately from the processor 118 and the memory 126. Other embodiments of the computing device 115 can have different, fewer, or additional components than shown in FIG. 1. In some embodiments, the computing device 115 can be a server. In other embodiments, the computing device 115 of FIG. 1 can be additionally connected to a server (e.g., as shown in FIG. 2 and discussed in greater detail below). The captured images/video can be processed or analyzed at the computing device 115 and/or a server to determine a variety of parameters (e.g., tidal volume, minute volume, respiratory rate, etc.) of a patient's breathing.

FIG. 2 is a block diagram illustrating a video-based patient monitoring system 200 (e.g., the video-based patient monitoring system 100 shown in FIG. 1) having a computing device 210, a server 225, and one or more image capture devices 285, and configured in accordance with various embodiments of the present technology. In various embodiments, fewer, additional, and/or different components can be used in the system 200. The computing device 210 includes a processor 215 that is coupled to a memory 205. The processor 215 can store and recall data and applications in the memory 205, including applications that process information and send commands/signals according to any of the methods disclosed herein. The processor 215 can also (i) display objects, applications, data, etc. on an interface/display 207 and/or (ii) receive inputs through the interface/display 207. As shown, the processor 215 is also coupled to a transceiver 220.

The computing device 210 can communicate with other devices, such as the server 225 and/or the image capture device(s) 285 via (e.g., wired or wireless) connections 270 and/or 280, respectively. For example, the computing device 210 can send to the server 225 information determined about a patient from images captured by the image capture device(s) 285. The computing device 210 can be the computing device 115 of FIG. 1. Accordingly, the computing device 210 can be located remotely from the image capture device(s) 285, or it can be local and close to the image capture device(s) 285 (e.g., in the same room). In various embodiments disclosed herein, the processor 215 of the computing device 210 can perform the steps disclosed herein. In other embodiments, the steps can be performed on a processor 235 of the server 225. In some embodiments, the various steps and methods disclosed herein can be performed by both of the processors 215 and 235. In some embodiments, certain steps can be performed by the processor 215 while others are performed by the processor 235. In some embodiments, information determined by the processor 215 can be sent to the server 225 for storage and/or further processing.

In some embodiments, the image capture device(s) 285 are remote sensing device(s), such as depth sensing video camera(s), as described above with respect to FIG. 1. In some embodiments, the image capture device(s) 285 can be or include some other type(s) of device(s), such as proximity sensors or proximity sensor arrays, heat or infrared sensors/cameras, sound/acoustic or radio wave emitters/detectors, or other devices that include a field of view and can be used to monitor the location and/or characteristics of a patient or a region of interest (ROI) on the patient. Body imaging technology can also be utilized according to the methods disclosed herein. For example, backscatter x-ray or millimeter wave scanning technology can be utilized to scan a patient, which can be used to define and/or monitor a ROI. Advantageously, such technologies can be able to "see" through clothing, bedding, or other materials while giving an accurate representation of the patient's skin. This can allow for more accurate measurements, particularly if the patient is wearing baggy clothing or is under bedding. The image capture device(s) 285 can be described as local because they are relatively close in proximity to a patient such that at least a part of a patient is within the field of view of the image capture device(s) 285. In some embodiments, the image capture device(s) 285 can be adjustable to ensure that the patient is captured in the field of view. For example, the image capture device(s) 285 can be physically movable, can have a changeable orientation (such as by rotating or panning), and/or can be capable of changing a focus, zoom, or other characteristic to allow the image capture device(s) 285 to adequately capture images of a patient and/or a ROI of the patient. In various embodiments, for example, the image capture device(s) 285 can focus on a ROI, zoom in on the ROI, center the ROI within a field of view by moving the image capture device(s) 285, or otherwise adjust the field of view to allow for better and/or more accurate tracking/measurement of the ROI.

The server 225 includes a processor 235 that is coupled to a memory 230. The processor 235 can store and recall data and applications in the memory 230. The processor 235 is also coupled to a transceiver 240. In some embodiments, the processor 235, and subsequently the server 225, can communicate with other devices, such as the computing device 210 through the connection 270.

The devices shown in the illustrative embodiment can be utilized in various ways. For example, either the connections 270 and 280 can be varied. Either of the connections 270 and 280 can be a hard-wired connection. A hard-wired connection can involve connecting the devices through a USB (universal serial bus) port, serial port, parallel port, or other type of wired connection that can facilitate the transfer of data and information between a processor of a device and a second processor of a second device. In another embodiment, either of the connections 270 and 280 can be a dock where one device can plug into another device. In other embodiments, either of the connections 270 and 280 can be a wireless connection. These connections can take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication can include near-field communications, such as passive radio-frequency identification (RFID) and active RFID technologies. RFID and similar near-field communications can allow the various devices to communicate in short range when they are placed proximate to one another. In yet another embodiment, the various devices can connect through an internet (or other network) connection. That is, either of the connections 270 and 280 can represent several different computing devices and network components that allow the various devices to communicate through the internet, either through a hard-wired or wireless connection. Either of the connections 270 and 280 can also be a combination of several modes of connection.

The configuration of the devices in FIG. 2 is merely one physical system 200 on which the disclosed embodiments can be executed. Other configurations of the devices shown can exist to practice the disclosed embodiments. Further, configurations of additional or fewer devices than the devices shown in FIG. 2 can exist to practice the disclosed embodiments. Additionally, the devices shown in FIG. 2 can be combined to allow for fewer devices than shown or can be separated such that more than the three devices exist in a system. It will be appreciated that many various combinations of computing devices can execute the methods and systems disclosed herein. Examples of such computing devices can include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Figure 3:
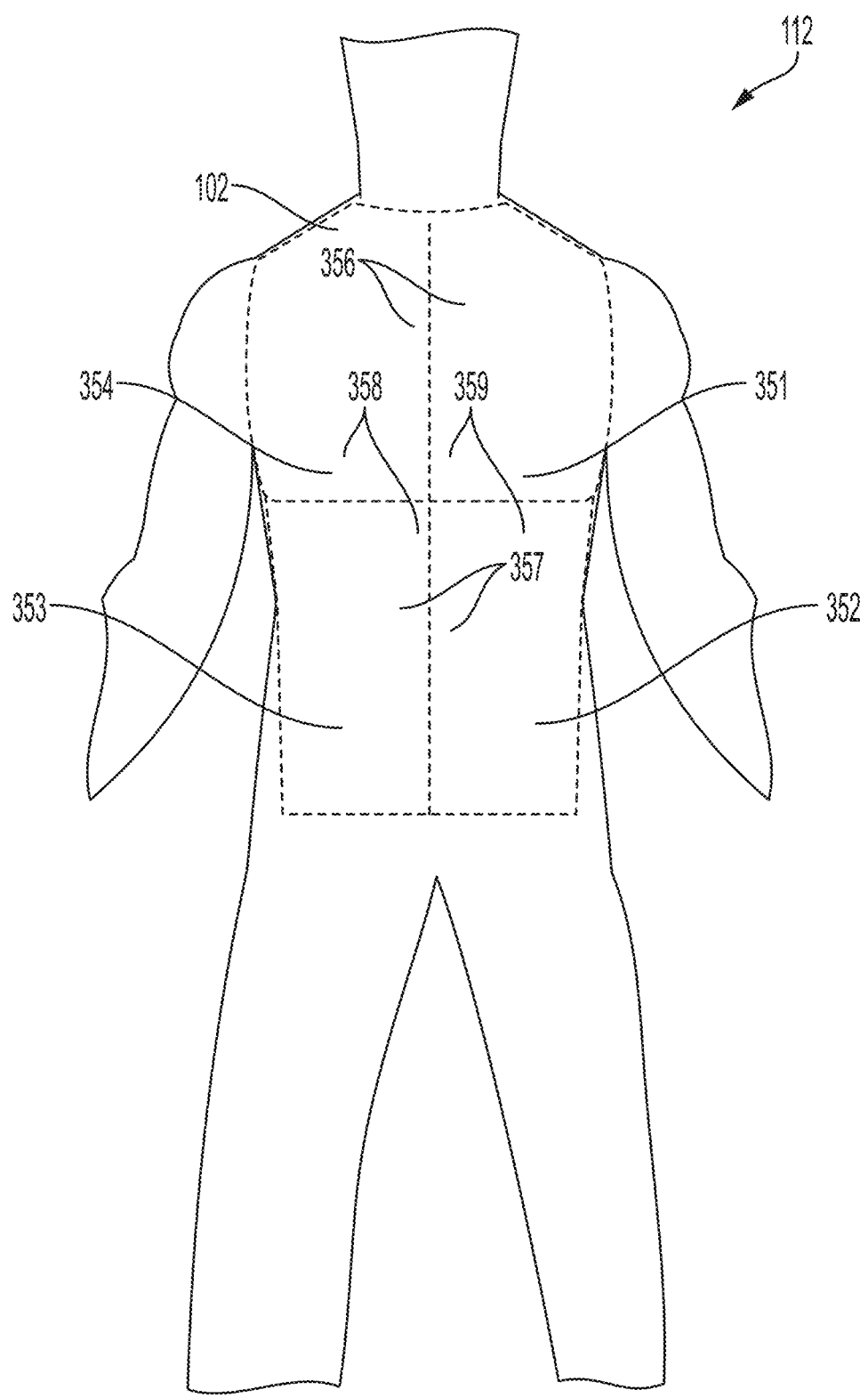
FIG. 3 is a schematic view of a patient showing various regions of interest that can be defined by video-based patient monitoring systems configured in accordance with various embodiments of the present technology.

FIG. 3 is a schematic view of a patient 112 showing various regions of interest (ROI's) that can be defined by video-based patient monitoring systems configured in accordance with various embodiments of the present technology. As discussed above, a video-based patient monitoring system can define a ROI using a variety of methods (e.g., using extrapolation from a point on the patient 112, using inferred positioning from proportional and/or spatial relationships with the patient's face, using parts of the patient 112 having similar depths from the camera 114 as a point, using one or more features on the patient's clothing, using user input, etc.). In some embodiments, the video-based patient monitoring system can define an aggregate ROI 102 that includes both sides of the patient's chest as well as both sides of the patient's abdomen. As discussed in greater detail below, the aggregate ROI 102 can be useful in determining a patient's aggregate tidal volume, minute volume, and/or respiratory rate, among other aggregate breathing parameters. In these and other embodiments, the system 100 can define one or more smaller regions of interest within the patient's torso.

For example, the system 100 can define ROI's 351-354. As shown, ROI 351 corresponds to the left half of the patient's chest, ROI 352 corresponds to the left half of the patient's abdomen, ROI 353 corresponds to the right half of the patient's abdomen, and ROI 354 corresponds to the right half of the patient's chest.

In these and other embodiments, the system 100 can define other regions of interest in addition to or in lieu of the ROI's 102, 351, 352, 353, and/or 354. For example, the system 100 can define a ROI 356 corresponding to the patient's chest (e.g., the ROI 351 plus the ROI 354) and/or a ROI 357 corresponding to the patient's abdomen (e.g., the ROI 352 plus the ROI 353). In these and other embodiments, the system 100 can define a ROI 358 corresponding to the right side of the patient's chest or torso (e.g., the ROI 353 and/or the ROI 354) and/or a ROI 359 corresponding to the left side of the patient's chest or torso (e.g., the ROI 351 and/or the ROI 352). In these and still other embodiments, the system 100 can define one or more other regions of interest than shown in FIG. 3. For example, the system 100 can define a region of interest that includes other parts of the patient's body, such as at least a portion of the patient's neck (e.g., to detect when the patient 112 is straining to breathe).

Figure 4A:
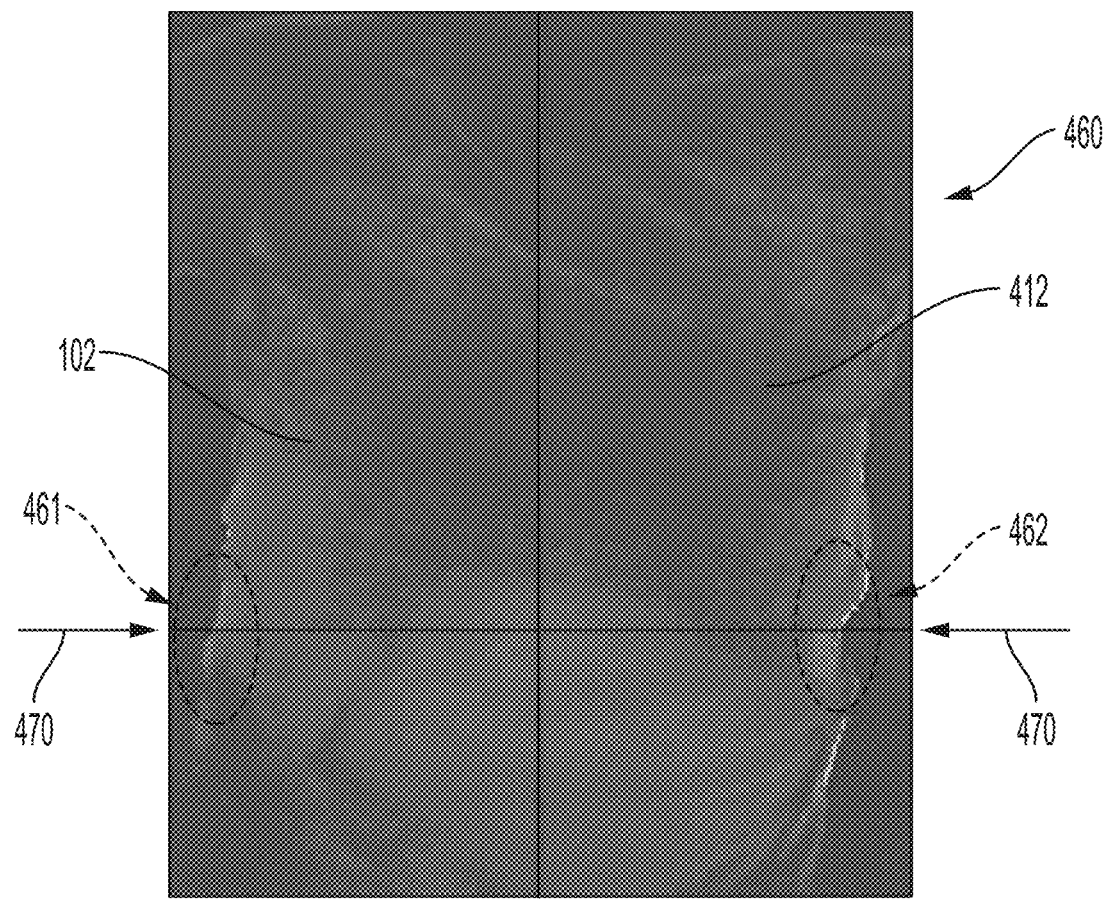
FIG. 4A is a false color depth sensing image of a region of interest corresponding to a patient's torso, captured using a video-based patient monitoring system configured in accordance with various embodiments of the present technology.

FIG. 4A is a false color depth sensing image 460 of a region of interest (ROI) 102 corresponding to a patient's torso 412. The image 460 can be captured using a video-based patient monitoring system configured in accordance with various embodiments of the present technology. In particular, the image 460 can be captured using an image capture device of the video-based patient monitoring system. The image capture device can include a field of view that is orthogonal to the patient's torso 412. The colors assigned to regions of the ROI 102 within the image 460 can correspond to exhibited changes in depths of the regions over time (e.g., across a previously captured image (not shown) of the ROI 102 and the image 460). For example, regions illustrated in lighter shades or colors in the image 460 can correspond to regions of the patient's torso 412 that the video-based patient monitoring system perceives exhibited larger magnitudes of changes in depths (e.g., in a particular direction) than other regions of the ROI 102 illustrated in darker shades or color. As shown in the image 460, the regions illustrated in lighter shades or colors include regions 461 and 462 of the ROI 102 that correspond to edges of the patient's torso 412.

Figure 4B:
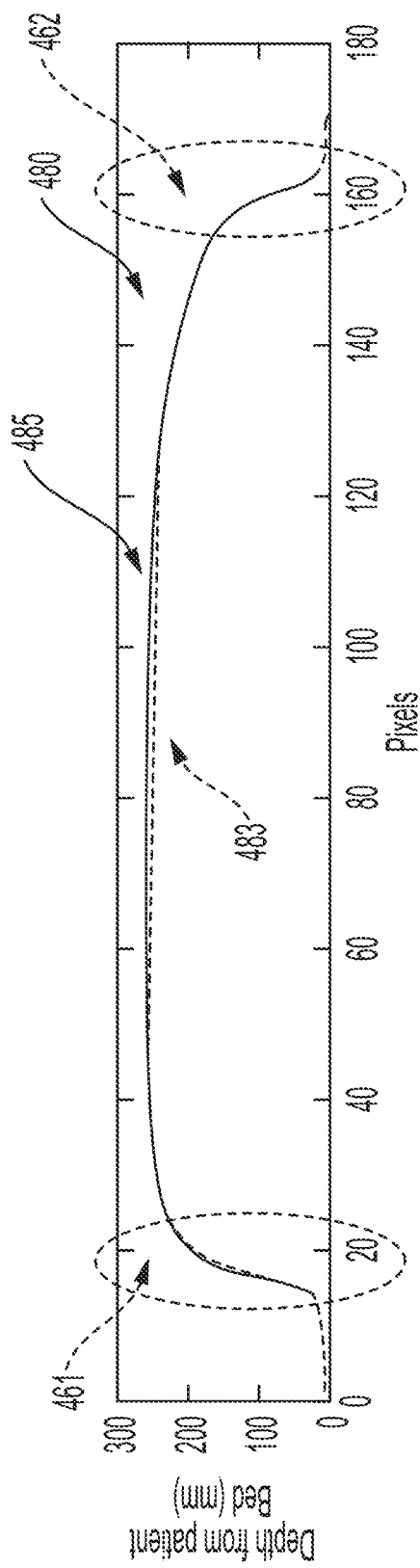
FIG. 4B is a line plot of depths measured across a portion of the depth sensing image of FIG. 4A.

FIG. 4B is a line plot 480 of depths measured across a horizontal portion 470 (FIG. 4A) of the depth sensing image 460 of FIG. 4A. As shown, the line plot 480 includes a depth curve 483 corresponding to depths measured across the portion 470 in an image (not shown) captured prior to the image 460 of FIG. 4A. The line plot 480 also includes a depth curve 485 that corresponds to depths measured across the portion 470 in the image 460. Differences between the curves 483 and 485 represent changes in depths of the corresponding pixels across the previously captured image and the image 460. Thus, regions within the line plot 480 where gaps are noticeably visible between the depth curve 483 and the depth curve 485 correspond to regions of the ROI 102 (FIG. 4A) where an image capture device detected large changes in depths across the previously captured image and the image 460. As shown, these regions of the line plot 480 include portions of the depth curves 483 and 485 that correspond to the edge regions 461 and 462 of the ROI 102 illustrated in FIG. 4B.

Figure 4C:
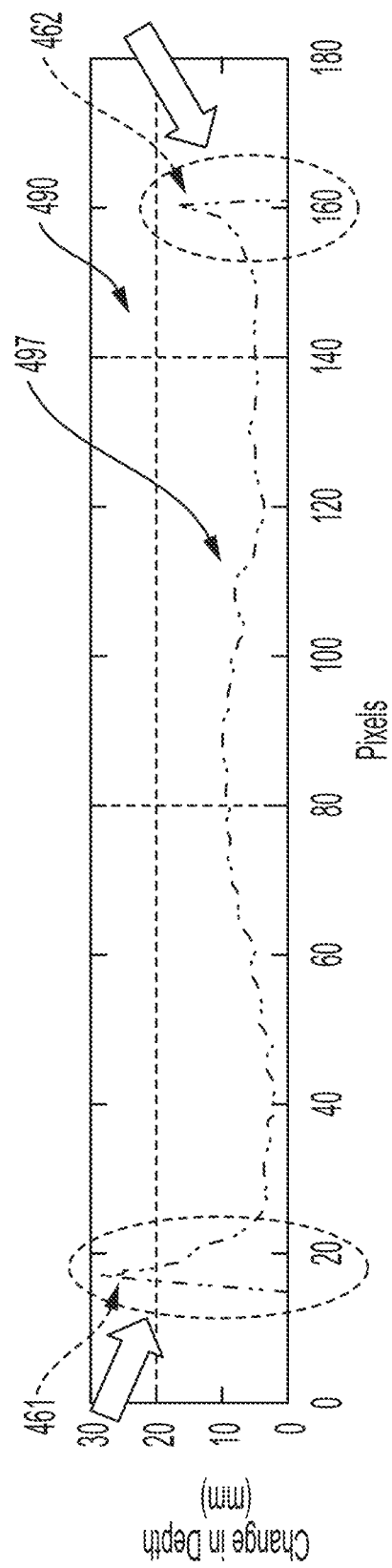
FIG. 4C is a line plot of a change in depth measured across a portion of the depth sensing image of FIG. 4A.

FIG. 4C is a line plot 490 illustrating measured changes in depths across the portion 470 of the depth sensing image 460 of FIG. 4A. In particular, the line plot 490 includes a change in depth curve 497 corresponding to the difference between the depth curve 485 and the depth curve 483 illustrated in FIG. 4B. As shown, the change in depth curve 497 includes large peaks at portions of the change in depth curve 497 that correspond to the edge regions 461 and 462 of the ROI 102 illustrated in FIG. 4A. These large peaks are caused by large gradients that exist at the edges of the ROI 102 and represent large changes in depths measured by the system at the edge regions of the patient's torso 412. The large changes in depths measured by the system, however, can inaccurately represent actual changes in depths of the patient's torso 412 at these regions for reasons discussed in greater detail below with respect to FIGS. 5A-5C. Thus, subsequent breathing parameters that are determined by the system using the change in depth curve 497 and/or the depth curves 583 and/or 585 can include errors introduced by the large, inaccurate measurements at regions of the depth curve 497 that correspond to edges of the patient's torso 412.

Figure 5A:
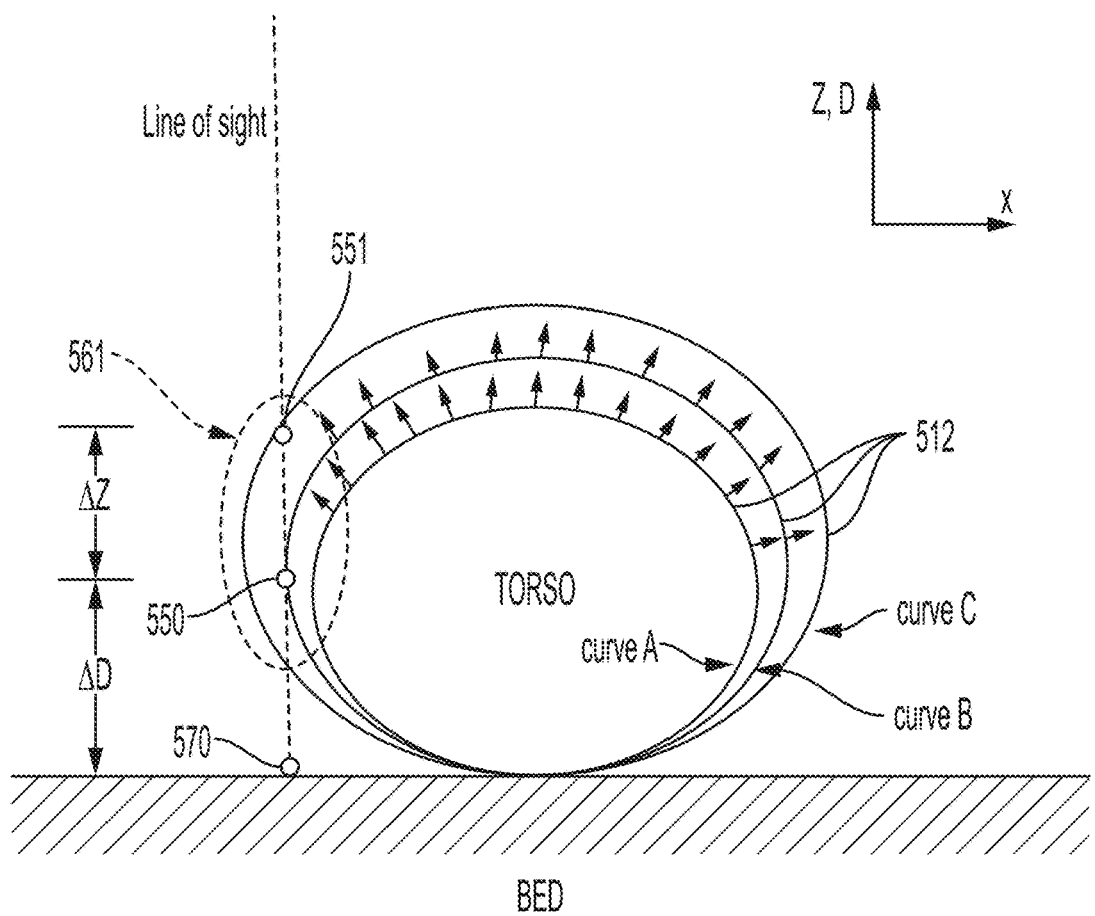
FIG. 5A is a schematic diagram of lateral movement of a patient's torso.

FIG. 5A is a schematic diagram of lateral movement of a patient's torso 512. In particular, FIG. 5A illustrates three curves (curves A, B, and C) of the patient's torso 512 on a patient bed 520, where each of the curves A, B, and C represents the patient's torso 512 at a respective stage within the patient's breathing cycle. The patient's torso 512 includes an edge region 561 within a field of view of an image capture device configured in accordance with various embodiments of the present technology. As shown, a line of sight within the field of view of the image capture device is oriented substantially orthogonal to the edge region 561 of the patient's torso 512 and/or to the patient bed 520.

Figure 5B:
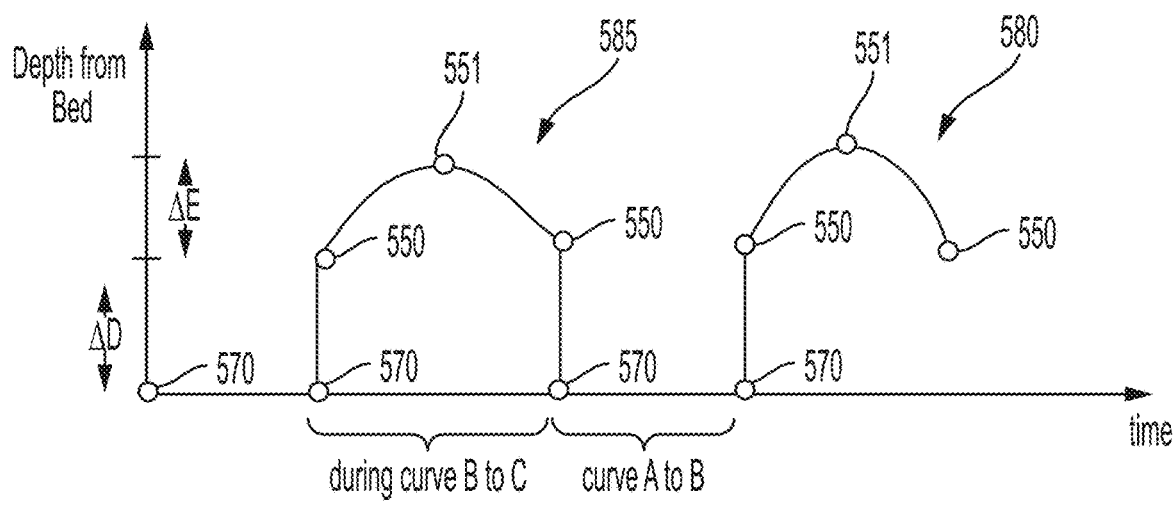
FIG. 5B is a line plot of measured depths of a patient's torso over time and generated using a non-contact patient monitoring system configured in accordance with various embodiments of the present technology.

FIG. 5B is a line plot 580 of measured depths of the patient's torso 512 (FIG. 5A) over time and generated using a non-contact patient monitoring system configured in accordance with various embodiments of the present technology. In particular, the line plot 580 includes a depth curve 585 that illustrates perceived depths of the patient's torso 512 (from the perspective of the image capture device and along the line of sight illustrated in FIG. 5A) relative to the patient bed 520 (FIG. 5A). Referring to FIGS. 5A and 5B together, a point 570 on the patient bed 520 is visible within the line of sight of the image capture device while the patient's torso 512 is represented by the curve A. Thus, at any point within the patient's breathing cycle where the patient's torso 512 can accurately be represented by the curve A or other curves between the curve A and the curve B, the image capture device perceives no difference in depth between the patient's torso 512 and the patient bed 520 along the line of sight. Accordingly, a first portion of the depth curve 585 illustrated in FIG. 5B (e.g., the initial portion between the point 570 and the point 570 on the curve 585) indicates that there is no distance between the patient's torso 512 and the patient bed 520.

As the patient's torso 512 illustrated in FIG. 5A moves laterally outward from the curve A to the curve B (e.g., as the patient inhales), the patient's torso 512 eventually blocks the point 570 on the patient bed 520 from being visible to the image capture device along the line of sight. Instead, the image capture device views a point 550 along the curve B of the patient's torso 512 within the line of sight. Thus, from the perspective of the image capture device, the patient's torso 512 appears to have suddenly jumped toward the image capture device and away from the patient bed 520 a distance ΔD representative of the distance between the patient bed 520 and the point 550 along the line of sight. In other words, as a result of lateral movement of the patient's torso 512 from the curve A to the curve B, the image capture device perceives a sudden change in depth of the patient's torso equal to the distance ΔD. Accordingly, this perceived change in depth is illustrated as a sudden jump on the depth curve 585 illustrated in FIG. 5B (e.g., by the portion of the curve 585 between the points 570 and 550). This perceived change in depth of the patient's torso 512, however, does not accurately represent the actual change in depth exhibited by the patient's torso 512 because not all of the perceived motion toward the image capture device can be attributed to the patient's torso 512.

Figure 5C:
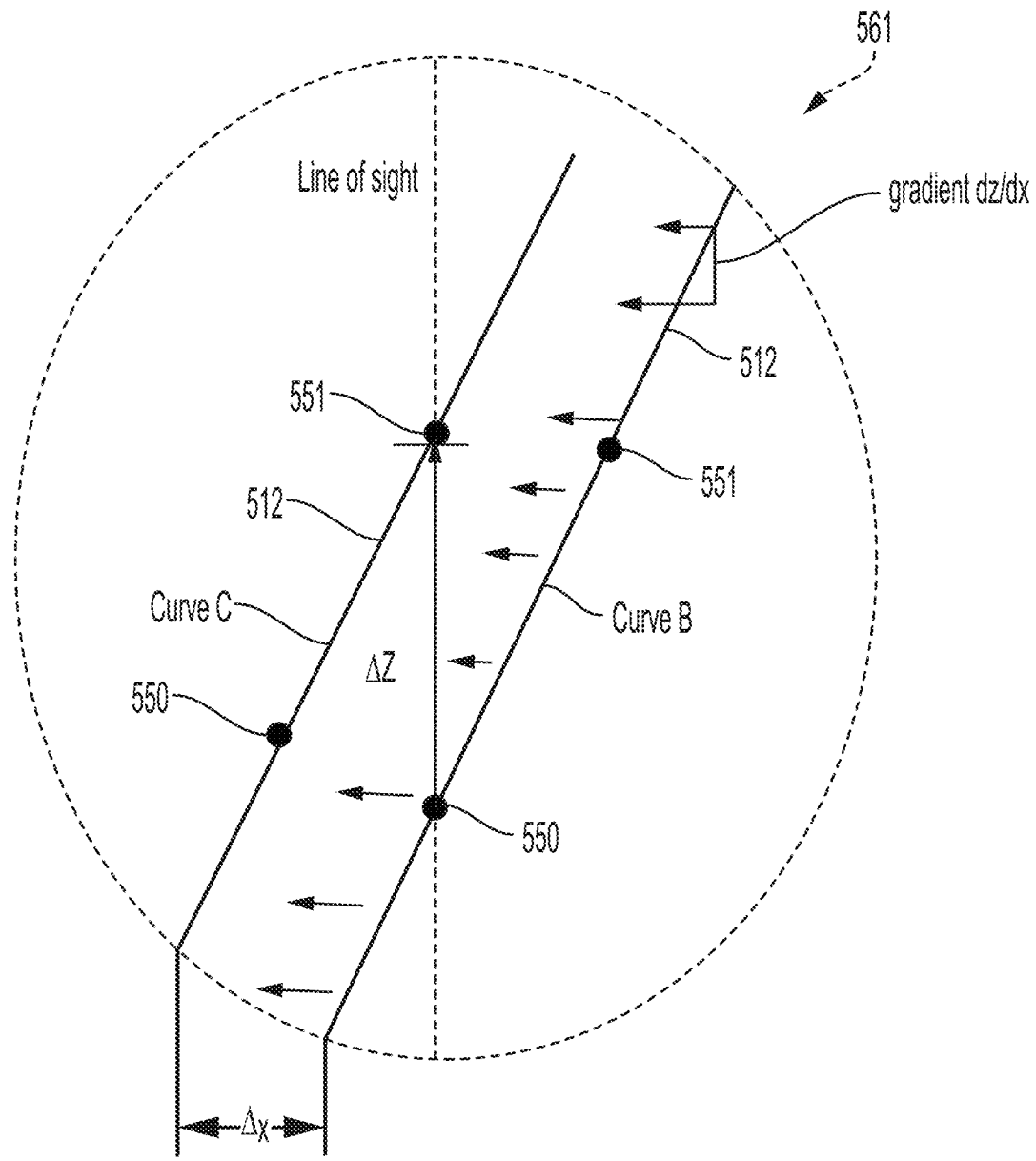
FIG. 5C is a schematic diagram of lateral movement of a patient's torso.

FIG. 5C is a schematic diagram illustrating a zoomed in view of the edge region 561 illustrated in FIG. 5A. In particular, FIG. 5C illustrates a portion of the edge region 561 that includes only the curves B and C of the patient's torso 512. As shown, the point 550 along the curve B is within the line of sight of the image capture device. As the patient's torso 512 moves laterally a distance ΔX in the direction illustrated by the arrows in FIG. 5C (e.g., as the patient inhales and the patient's torso 512 expands from the curve B to the curve C), the point 550 of the patient's torso 512 moves outside of the line of sight of the image capture device while the point 551 along the curve C of the patient's torso 512 moves within the light of sight of the image capture device. From the perspective of the image capture device, the patient's torso 512 has moved toward the image capture device a distance ΔZ along the line of sight of the image capture device. In other words, the image capture device perceives a large change in depth of the patient's torso 512 up the gradient ΔZ/ΔX as a result of a slight, lateral translation of the patient's torso 512 from the curve B to the curve C. This change in depth is illustrated as the first half of the concave parabola of the depth curve 585 illustrated in FIG. 5B (e.g., by the portion of the curve 585 between the point 550 and the point 551). The large, perceived change in depth of the patient's torso 512, however, similarly does not accurately represent the actual change in depth exhibited by the patient's torso 512 because not all of the perceived motion toward the image capture device can be attributed to the same portion of the patient's torso 512.

As the patient exhales, similar changes in depths (but in the opposite direction) are perceived by the image capture device along the line of sight. For example, the same large, perceived change in depth away from the image capture device can occur as the patient's torso 512 moves in the opposite direction than illustrated in FIG. 5C (e.g., as the patient exhales and the patient's torso 512 deflates from the curve C to the curve B). Thus, lateral movement of the patient's torso 512 can again translate to large, inaccurate changes in depths perceived by the image capture device at the edge region 561 of the patient's torso 512. This change in depth is illustrated as the second half of the concave parabola of the depth curve 585 illustrated in FIG. 5B (e.g., by the portion of the curve 585 between the point 551 and the point 550). Similarly, the same, sudden jump in depth (but away from the image capture device and toward the patient bed 520) can occur as the patient's torso 512 moves in the opposite direction than illustrated in FIG. 5A (e.g., as the patient exhales and the patient's torso 512 deflates from the curve B to the curve A). That is, as the patient's torso 512 moves outside of the line of sight of the image capture device, the point 570 on the patient bed 520 again becomes visible to the image capture device along the line of sight. The corresponding, perceived change in depth is illustrated as a sudden jump on the depth curve 585 illustrated in FIG. 5B (e.g., by the portion of the curve 585 between the points 550 and 570). Each of the above errors can repeatedly occur over several cycles of the patient's breathing, as shown by the depth curve 585 illustrated in FIG. 5B.

Therefore, as discussed above, the large changes in depths measured by the system at edge regions of a patient within a line of sight of an image capture device can inaccurately represent actual changes in depths exhibited by these regions. In turn, patient respiratory parameters that are determined at least in part using these large, perceived changes in depths (without correction) can be inaccurate. Accordingly, video-based patient monitoring devices, systems, and methods configured in accordance with various embodiments of the present technology are configured to account for the inaccuracy of changes in depths perceived at edge regions of a patient, thereby increasing accuracy of the subsequently determined patient respiratory parameters.

Figure 6:
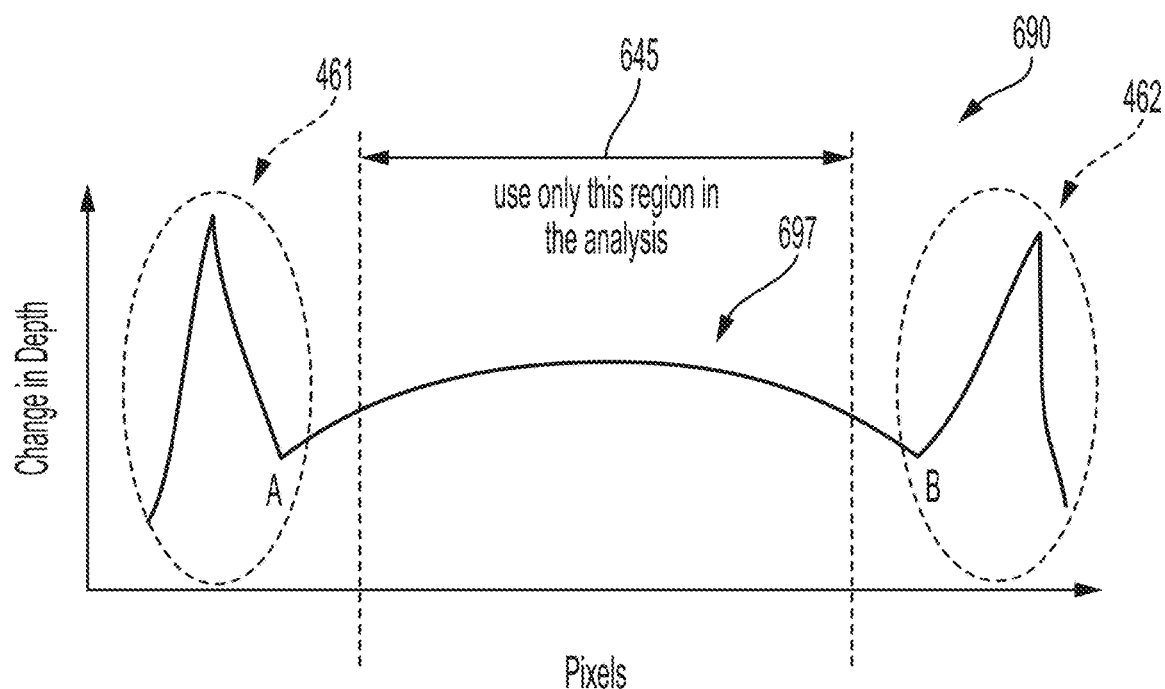
FIGS. 6-8 are line plots illustrating various methods for mitigating errors resulting from changes in depths perceived at edges of a patient's torso in accordance with various embodiments of the present technology.
Figure 7:
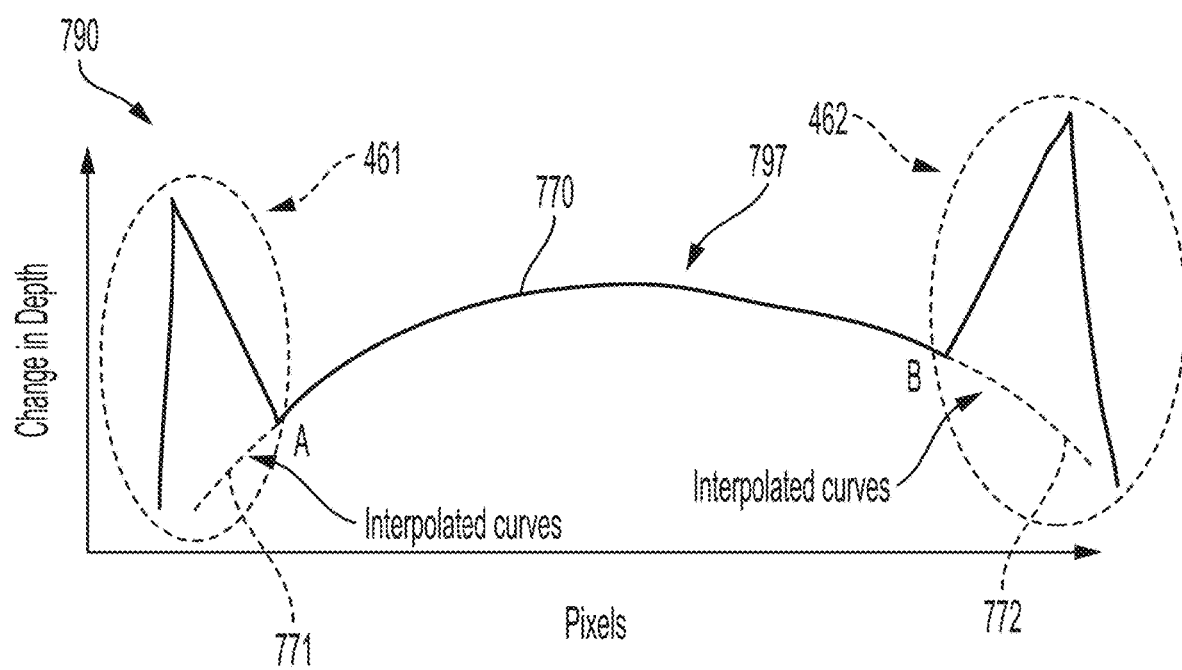
Figure 8:
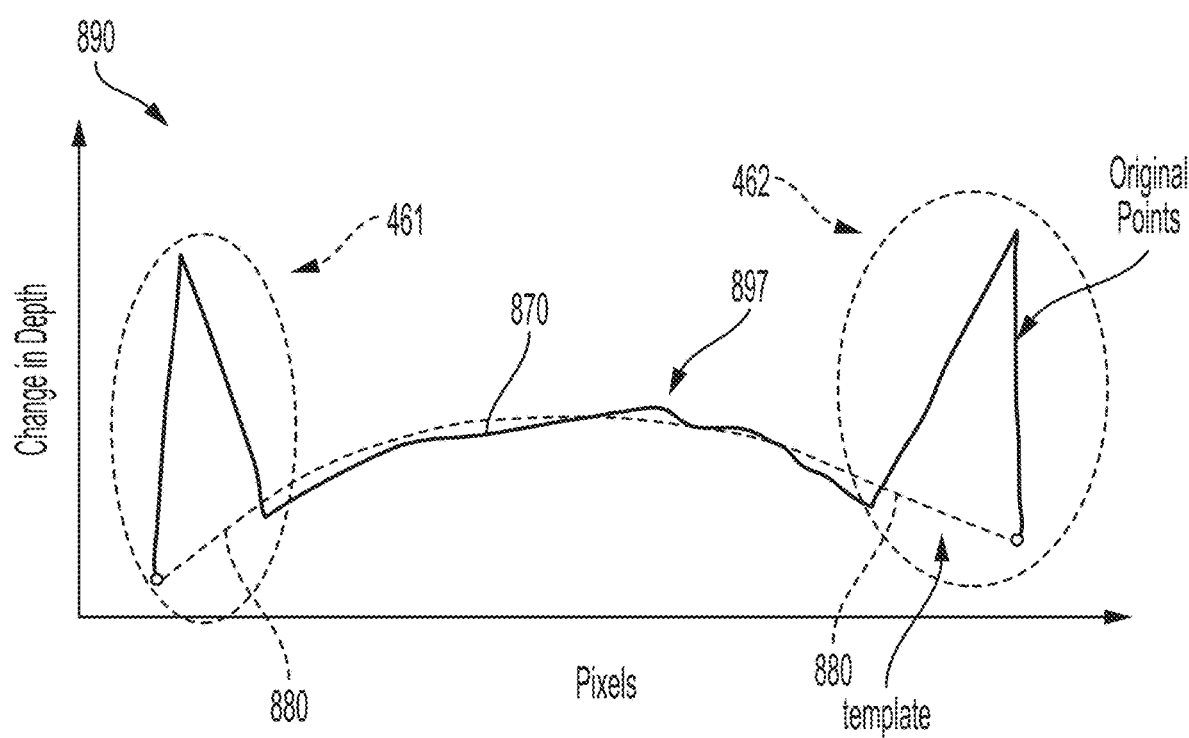

FIGS. 6-8 are line plots 690, 790, and 890, respectively, illustrating various methods for mitigating errors resulting from changes in depths perceived at edges of a patient's torso in accordance with various embodiments of the present technology. The line plots 690, 790, and 890 are similar to the line plot 490 illustrated in FIG. 4C. For example, the line plots 690, 790, and 890 each include a change in depth curve 697, 797, and 897, respectively, similar to the change in depth curve 497 (FIG. 4B). That is, each of the change in depth curves 697, 797, and 897 illustrate changes in depths perceived by an image capture device across the horizontal portion 470 of the depth image 460 illustrated in FIG. 4A. In addition, each of the change in depth curves 696, 797, and 897 includes large peaks (representing large changes in depths) at portions of the change in depth curves 697, 797, and 897 that correspond to edge regions 461 and 462 of the ROI 102 and the patient's torso 512 illustrated in FIG. 4A. As discussed above with respect to FIGS. 5A-5C, these large peaks are caused by large gradients that exist at the edges of the ROI 102 and represent large changes in depths perceived by the system at the edge regions of the patient's torso 412.

Referring to FIG. 6, to calculate the total change in depth of the patient's torso across the portion 470 of the image 460 illustrated in FIG. 4A, video-based patient monitoring devices, systems, and methods configured in accordance with the present technology can integrate over a region of the change in depth curve 696 within the extent of the patient's torso 412. For example, the devices, systems, and methods can integrate over only a portion 645 of the change in depth curve 697. The portion 645 of the change in depth curve 697 can be defined as a subset of the curve 697 (e.g., the inner 80 to 90 percent of the curve 697 such that the outer five to ten percent of the curve at either end is left out of the integration). In these and other embodiments, the devices, systems, and methods can recognize steep gradients and rapid changes in depths (e.g., the devices, systems, and methods can recognize the large peaks along the change in depth curve 697). In these embodiments, the devices, systems, and methods can define the portion 645 of the curve 697 for use in the integration. For example, the devices, systems, and methods can define the portion 645 as the portion of the curve 697 between the points A and B in FIG. 6 after recognizing the sharp increase in depths or changes in depths beginning at these points A and B. In this manner, the devices, system, and methods of the present technology can prevent introducing the large, perceived changes in depths in the edge regions 461 and/or 462 in the determination of a patient's respiratory parameters.

In these and other embodiments, the video-based patient monitoring devices, systems, and methods can interpolate points between (i) a location on a change in depth curve corresponding to a location near to the edge of a patient's torso and (ii) a location on the change in depth curve corresponding to a location of the edge of the patient's torso. Referring to FIG. 7, for example, the devices, systems, and methods can determine where sharp changes in depths occur (e.g., the devices, systems, and methods can determine where the points A and/or B are located along the change in depth curve 797). From the points A and/or B, the devices, systems, and methods can interpolate points to the end(s) of the curve 797, to zero, or to another value (e.g., using a curve fitted to one or more inner portions 770 of the curve 797). For example, the devices, systems, and methods can fit a curve to all or a subset of the points along the portion 770 of the curve 797 and interpolate points to the left end of the curve 797 to generate an end portion 771 of the curve 797. Additionally, or alternatively, the devices, systems, and methods can fit a curve to all or a subset of the points along the portion 770 of the curve 797 and interpolate points to the right end of the curve 797 to generate an end portion 772 of the curve 797. In these embodiments, the interpolated portions 771 and/or 772 of the curve 797 can be included in the integration to calculate the total change in depth of the patient's torso 412. As a result, an approximation of the changes in depths that are exhibited by the patient within the edge regions 461 and/or 462 can be included in the integration without inserting the large, inaccurate changes in depths perceived by an image capture device in the determination of a patient's respiratory parameters.

In these and still other embodiments, the video-based patient monitoring devices, systems, and methods can fit a template to one or more points along a change in depth curve. Referring to FIG. 8, for example, the devices, systems, and methods can fit a template 880 to one or more points along an inner portion 870 of the change in depth curve 897. In some embodiments, the template 880 can be a default template (e.g., used for all patients). In these and other embodiments, the template 880 can be generated as an aggregate shape from a population-based analysis of body shapes. In these and still other embodiments, the template 880 can be generated from a prior body scan of the patient. In some embodiments, the template 880 can correspond to a current position along the patient's respiratory cycle.

As shown in FIG. 8, the template 880 can perform a similar function as the interpolation illustrated in FIG. 7. For example, the template 880 can exclude the large, perceived changes in depths along the change in depth curve 897 from an integration of the total change in depth of the patient's torso 412, and can instead insert an approximation of the changes in depths exhibited by the patient's torso 412 within the edge regions 461 and/or 462. As a result, the accuracy of patient respiratory parameters determined at least in part using measured changes in depths can be increased.

In other embodiments, the video-based patient monitoring devices, systems, and methods can include multiple image capture devices. In these embodiments, an image capture device can remain substantially orthogonal to a region of interest on a patient (e.g., to the patient's torso), and one or more other image capture devices can be positioned at other angles offset from 90 degrees to the region of interest. In this manner, the other image capture device(s) can view around the edge regions of the region of interest and/or can be positioned such that lateral movement of the patient is directed toward or away from the other image capture device(s). Thus, data captured by the other images capture device(s) can be used to factor or filter out and/or account for the large, inaccurate changes in depths perceived at edge portions of the patient by the substantially orthogonal image capture device.

While the foregoing discussion used a horizontal portion 470 (FIG. 4A) of the depth sensing image 460 (FIG. 4A), other horizontal portions and/or other portions at other angles across the depth sensing image 460 in addition to or in lieu of the portion 470 can be used in these and other embodiments. Furthermore, in some embodiments, a two-dimensional surface corresponding to all or a subset of the image 460 can be used. In these embodiments, the two-dimensional surface may be interrogated to locate rapid changes in depths (e.g., steep gradients). Once located, the rapid changes in depths can be accounted for in accordance with the discussion of any of the foregoing embodiments.

Figure 9:
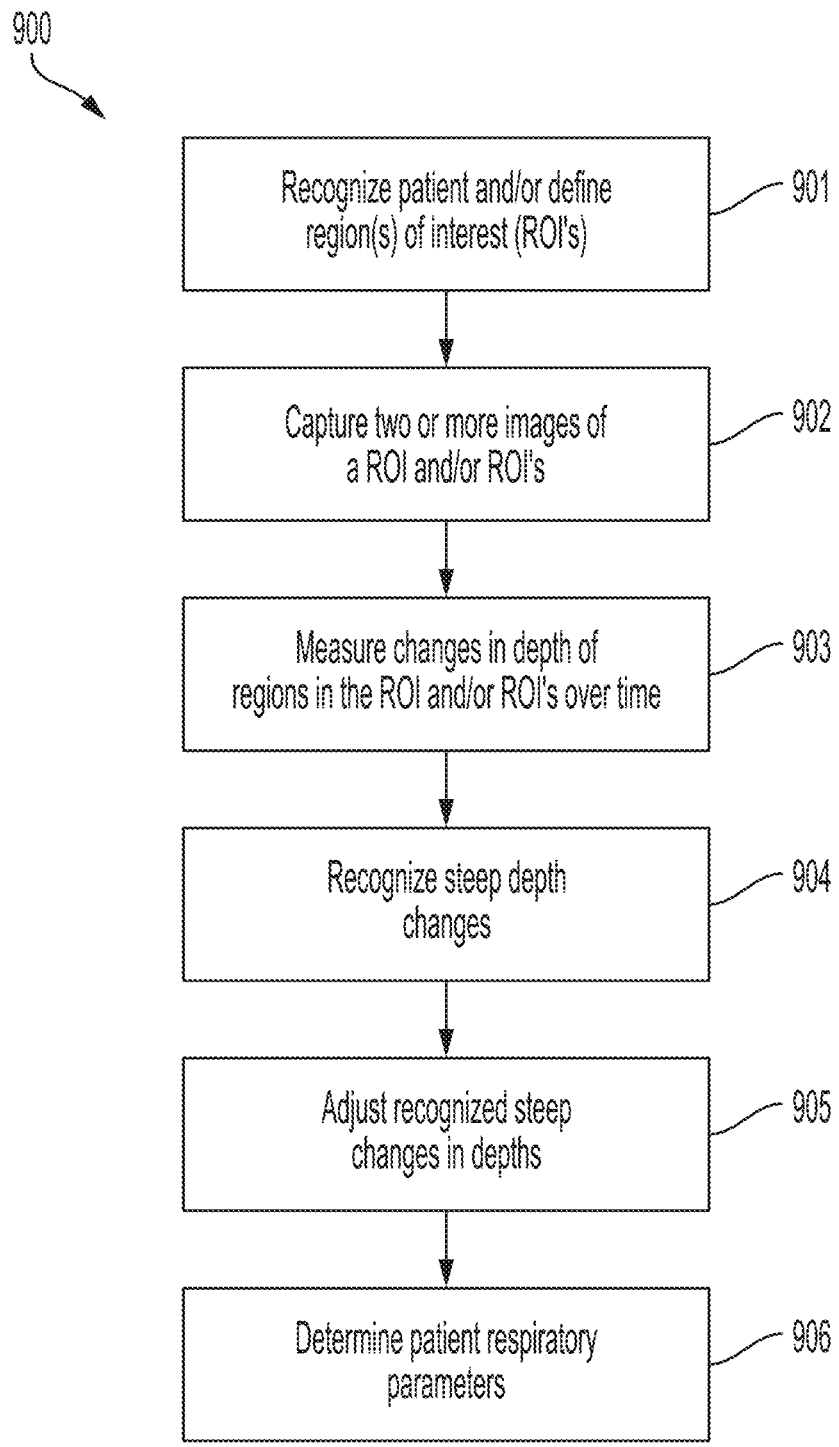
FIG. 9 is a flow diagram illustrating a method for mitigating errors in changes in depths measured at edge regions of a patient in accordance with various embodiments of the present technology.

FIG. 9 is a flow diagram illustrating a routine 900 for mitigating errors in changes in depths measured at edge regions of a patient in accordance with various embodiments of the present technology. All or a subset of the steps of the routine 900 can be executed by various components or devices of a video-based patient monitoring system and/or a user of the system (e.g., a caregiver, a clinician, a patient, etc.). For example, all or a subset of the steps of the routine 900 can be executed by (i) components or devices of the video-based patient monitoring system 100 shown in FIG. 1 and/or (ii) components or devices of the video-based patient monitoring system 200 shown in FIG. 2.

The routine 900 can begin at block 901 by recognizing a patient within a field of view (FOV) of the image capture device and/or by defining one or more regions of interest (ROI's) on the patient. In some embodiments, the routine 900 can recognize the patient by identifying the patient using facial recognition hardware and/or software of the image capture device. In these embodiments, the routine 900 can display the name of the patient on a display screen once the routine 900 has identified the patient. In these and other embodiments, the routine 900 can recognize a patient within the FOV of the image capture device by determining a skeleton outline of the patient and/or by recognizing one or more characteristic features (e.g., a torso of a patient). In these and still other embodiments, the routine 900 can define one or more ROI's on the patient in accordance with the discussion above with respect to FIGS. 1 and/or 3. For example, the routine 900 can define one or more ROI's on the patient using extrapolation from a point on the patient, using inferred positioning from proportional and/or spatial relationships with the patient's face, using parts of the patient having similar depths from the camera 114 as a point, using one or more features on the patient's clothing, using user input, etc.

At block 902, the routine 900 can capture two or more images of one or more ROI's. In some embodiments, the routine 900 can capture the two or more images of the one or more ROI's by capturing a video sequence of the one or more ROI's. In these and other embodiments, the routine 900 can capture the two or more images of the one or more ROI's by capturing separate still images of the one or more ROI's. The routine 900 can capture the two or more still images at a rate faster than a period of the patient's respiration cycle to ensure that the two or more still images occur within one period of the patient's respiration cycle.

At block 903, the routine 900 can measure changes in depths of one or more regions in one or more ROI's over time. In some embodiments, the routine 900 can measure changes in depths of regions in the one or more ROI's by computing a difference between a depth of a region of a ROI in a first captured image of the ROI and a depth of the same region in a second captured image of the ROI.

At block 904, the routine 900 can recognize steep changes (increases and/or decreases) in depths measured at block 903. In some embodiments, the routine 900 can interrogate all or a subset of the changes in depths measured at block 903 to locate steep changes in depths. For example, the routine 900 can interrogate all or a subset of a two-dimensional surface corresponding to all or a subset of the changes in depths measured at block 903. In these and other embodiments, the routine 900 can interrogate a portion of the changes in depths measured at block 903, such as a horizontal portion, a vertical portion, a portion at another angle, a portion the routine 900 recognizes corresponds to an edge region of the ROI's and/or the patient, etc. In these and still other embodiments, the routine 900 can recognize a steep change in depth as a change in depth having a magnitude greater than or equal to a threshold value (e.g., greater than or equal to a predefined value or a value dependent on the patient).

At block 905, the routine 900 can adjust the steep changes in depths measured at block 903 and/or recognized at block 904. In some embodiments, the routine 900 can adjust the steep changes in depths by excluding them from subsequent calculations (e.g., excluding them from calculations used to determine a patient's respiratory parameters at block 906). For example, the routine 900 can exclude the steep changes in depths from a subsequent integration to determine an overall change in depth exhibited across all or a portion of the changes in depths measured at block 903 (e.g., by integrating within the extent of a patient's torso). In these embodiments, the routine 900 can include only changes in depths within an inner percentage of all or a subset of the measured changes in depths (e.g., within an inner percentage of regions corresponding to a patient's torso) in the integration such that an outer percentage near edge regions of the patient are excluded from the integration. In these and other embodiments, the routine 900 can include all measured changes in depths up to and/or between recognized steep changes in depths.

In some embodiments, the routine 900 can use one or more measured changes in depths to interpolate or extrapolate one or more changes in depths over the recognized steep changes in depths (e.g., by using one or more curves and/or one or more changes in depths measured at block 903). In these and other embodiments, the routine 900 can use a template to approximate changes in depths exhibited by regions that correspond to recognized steep changes in depths. The template can be a default template or a template based on a prior body scan of the patient. In these and other embodiments, the template can be an aggregate shape determined from a population-based analysis of body shapes. In these and still other embodiments, the template can correspond to a current position along the patient's respiratory cycle and/or can correspond to one or more changes in depths measured at block 903. In these and yet other embodiments, the routine 900 can use data captured by one or more other, non-orthogonal image capture devices to filter or factor out and/or account for the recognized steep changes in depths perceived by an orthogonal image capture device.

At block 906, the routine 900 can determine one or more patient respiratory parameters using all or a subset of the changes in depths measured at block 903 and/or all or a subset of the adjusted changes in depths generated at block 905. For example, the routine 900 can determine a patient's tidal volume, minute volume, and/or respiratory rate, among others. In some embodiments, the routine 900 can calculate the patient's tidal volume using a subset of the changes in depths measured at block 903 and/or all or a subset of the adjusted changes in depths generated at block 905. In these and other embodiments, the routine 900 can calculate the patient's respiratory rate using all of the changes in depths measured at block 903 (including the recognized steep changes in depths) and none of the adjusted changes in depths generated at block 905 (as the recognized steep changes in depths can be clear markers in a time signal of a respiratory signal).

Although the steps of the routine 900 are discussed and illustrated in a particular order, the routine 900 in FIG. 9 is not so limited. In other embodiments, the routine 900 can be performed in a different order. In these and other embodiments, any of the steps of the routine 900 can be performed before, during, and/or after any of the other steps of the routine 900. Moreover, a person of ordinary skill in the relevant art will readily recognize that the illustrated method can be altered and still remain within these and other embodiments of the present technology. For example, one or more steps of the routine 900 illustrated in FIG. 9 can be omitted and/or repeated in some embodiments.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A method, comprising:
    defining a region of interest (ROI) on a patient;
    capturing two or more images of the ROI using an image capture device;
    calculating an overall change in depth of the ROI within the two or more images, wherein calculating the overall change in depth of the ROI includes:
        measuring changes in depths of portions of the ROI;
        recognizing steep changes in depths in the measured changes in depths; and
        adjusting the recognized steep changes in depths;
    exclude the recognized steep changes in depths from the calculation of the overall change in depth of the ROI;
    exclude measured changes in depths corresponding to an outer percentage of the ROI and/or to an edge region of the patient;
    exclude a percentage of the measured changes in depths surrounding a recognized steep change in depth;
    include only measured changes in depths up to and/or between one or more recognized steep changes in depths in the calculation of the overall change in depth of the ROI;
    interpolate and/or extrapolate over the recognized steep changes in depths using one or more other measured changes in depths;
    use a template to approximate changes in depths at portions of the ROI corresponding to the recognized steep changes in depths; and/or
    adjust the recognized steep changes in depths using data captured by a second image capture device.

2. The method of claim 1, wherein adjusting the recognized steep changes in depths includes excluding the recognized steep changes in depths from the calculation of the overall change in depth of the ROI.

3. The method of claim 1, wherein adjusting the recognized steep changes in depths includes (i) excluding measured changes in depths corresponding to an outer percentage of the ROI and/or to an edge region of the patient and/or (ii) excluding a percentage of the measured changes in depths surrounding a recognized steep change in depth.

4. The method of claim 1, wherein adjusting the recognized steep changes in depths comprises including only measured changes in depths up to and/or between one or more recognized steep changes in depths in the calculation of the overall change in depth of the ROI.

5. The method of claim 1, wherein adjusting the recognized steep changes in depths includes interpolating and/or extrapolating over the recognized steep changes in depths using one or more other measured changes in depths.

6. The method of claim 1, wherein adjusting the recognized steep changes in depths includes using a template to approximate changes in depths at portions of the ROI corresponding to the recognized steep changes in depths.

7. The method of claim 6, wherein the template is a default template, the template is generated from a prior body scan of the patient, and/or the template is an aggregate shape determined from a population-based analysis of body shapes.

8. The method of claim 6, wherein the template corresponds to a current position within the patient's respiratory cycle and/or the template corresponds to one or more other measured changes in depths.

9. The method of claim 1, wherein the image capture device is a first image capture device, and wherein adjusting the recognized steep change in depths includes adjusting the recognized steep changes in depths using data captured by a second image capture device.

10. The method of claim 1, wherein recognizing the steep changes in depths includes identifying measured changes in depths having a magnitude greater than or equal to a threshold value.

11. The method of claim 10, wherein the threshold value is a predefined value and/or a value defined based on one or more previously measured changes in depths corresponding to the patient.

12. The method of claim 1, wherein recognizing the steep changes includes interrogating all or a subset of the measured changes in depths.

13. The method of claim 1, further comprising determining one or more patient respiratory parameters using all or a subset of the measured changes in depths and/or all or a subset of the adjusted changes in depths.

14. The method of claim 13, wherein the one or more patient respiratory parameters includes a tidal volume of the patient, and wherein the tidal volume of the patient is determined using a subset of the measured changes in depths excluding the recognized steep changes in depths and/or all or a subset of the adjusted changes in depths.

15. The method of claim 13, wherein the one or more patient respiratory parameters includes a respiratory rate of the patient, and wherein the respiratory rate of the patient is determined using all of the measured changes in depths and none of the adjusted changes in depths.

16. A video-based patient monitoring system, comprising:
at least one processor configured to define a region of interest (ROI) on a patient; and
a non-contact detector having at least a first image capture device, wherein:
at least the first image capture device is configured to capture two or more images of the ROI,
the at least one processor is further configured to calculate an overall change in depth of the ROI within the two or more images, and
to calculate the overall change in depth of the ROI within the two or more images, the at least one processor is further configured to:
measure changes in depths of portions of the ROI within the two or more images;
recognize steep changes in depths in the measured changes in depths; and
adjust the recognized steep changes in depths;
exclude the recognized steep changes in depths from the calculation of the overall change in depth of the ROI;
exclude measured changes in depths corresponding to an outer percentage of the ROI and/or to an edge region of the patient;
exclude a percentage of the measured changes in depths surrounding a recognized steep change in depth;
include only measured changes in depths up to and/or between one or more recognized steep changes in depths in the calculation of the overall change in depth of the ROI;
interpolate and/or extrapolate over the recognized steep changes in depths using one or more other measured changes in depths;
use a template to approximate changes in depths at portions of the ROI corresponding to the recognized steep changes in depths; and/or
adjust the recognized steep changes in depths using data captured by a second image capture device.

17. The video-based patient monitoring system of claim 16, wherein, to adjust the recognized steep changes in depths, the at least one processor is further configured to use a template to approximate changes in depths at portions of the ROI corresponding to the recognized steep changes in depths, and wherein the template is generated from a prior body scan of the patient and/or is an aggregated shape from a population-based analysis of body shapes.

18. The video-based patient monitoring system of claim 16, wherein, to recognize steep changes in depths in the measured changes in depths, the at least one processor is further configured to interrogate all or a subset of the measured changes in depths and to identify measured changes in depths having a magnitude greater than or equal to a threshold value.

19. The video-based patient monitoring system of claim 16, wherein the at least one processor is further configured to determine one or more patient respiratory parameters using all or a subset of the measured changes in depths and/or all or a subset of the adjusted changes in depths.

* * * * *